(12) United States Patent
Kassab et al.

(10) Patent No.: US 11,382,528 B2
(45) Date of Patent: Jul. 12, 2022

(54) LUMINAL IMPEDANCE DEVICE WITH INTEGRATED CIRCUIT MODULES

(71) Applicant: 3DT Holdings, LLC, San Diego, CA (US)

(72) Inventors: Ghassan S. Kassab, La Jolla, CA (US); Chris Minar, New Prague, MN (US); Orhan Soykan, Shoreview, MN (US); William Combs, Galena, OH (US)

(73) Assignee: 3DT Holdings, LLC, San Diego, CA (US)

( * ) Notice: Subject to any disclaimer, the term of this patent is extended or adjusted under 35 U.S.C. 154(b) by 215 days.

(21) Appl. No.: 16/674,990

(22) Filed: Nov. 5, 2019

(65) Prior Publication Data

US 2020/0060577 A1  Feb. 27, 2020

Related U.S. Application Data

(63) Continuation of application No. 15/115,586, filed as application No. PCT/US2015/013939 on Jan. 30, 2015, now Pat. No. 10,463,274.
(Continued)

(51) Int. Cl.
*A61B 5/053* (2021.01)
*A61B 5/0538* (2021.01)
(Continued)

(52) U.S. Cl.
CPC .......... *A61B 5/0538* (2013.01); *A61B 5/0022* (2013.01); *A61B 5/01* (2013.01);
(Continued)

(58) Field of Classification Search
CPC .......... A61B 5/053; A61B 5/0215; A61B 8/06
See application file for complete search history.

(56) References Cited

U.S. PATENT DOCUMENTS

| | | |
|---|---|---|
| 2004/0102722 A1 | 5/2004 | Naghavi |
| 2004/0230131 A1 | 11/2004 | Kassab |

(Continued)

FOREIGN PATENT DOCUMENTS

| | | | | |
|---|---|---|---|---|
| JP | 2015520641 A | * 7/2015 | ............... | A61B 8/06 |
| JP | 6240169 B2 | * 11/2017 | ............... | A61B 8/06 |
| WO | 98/35611 A1 | 8/1998 | | |

OTHER PUBLICATIONS

International Searching Authority, International Search Report and Written Opinion of the International Searching Authority, PCT/US2015/013939, dated May 1, 2015.

*Primary Examiner* — Michael J D'Abreu

(57) ABSTRACT

Impedance devices with integrated circuit modules and method of using the same to obtain luminal organ information. In one embodiment, a device comprises an elongated body for at least partial insertion into a mammalian luminal organ and having a first conductor extending therethrough, a proximal electrical unit connected to the elongated body to deliver power along the first conductor, and a sensor substrate located at or near a distal end of the elongated body and comprising a circuit module operable and/or configured to direct the sizing portion to obtain sizing data and the pressure sensor to obtain pressure data, and facilitate transmission of the sizing data and/or the pressure data to the proximal electrical unit.

20 Claims, 24 Drawing Sheets

Related U.S. Application Data

(60) Provisional application No. 61/933,803, filed on Jan. 30, 2014.

(51) Int. Cl.
*A61B 5/00* (2006.01)
*A61B 5/01* (2006.01)
*A61B 5/0215* (2006.01)
*A61B 5/0205* (2006.01)
*A61B 5/026* (2006.01)
*A61B 5/107* (2006.01)
*A61B 5/027* (2006.01)
*A61B 5/03* (2006.01)

(52) U.S. Cl.
CPC ............ *A61B 5/0205* (2013.01); *A61B 5/026* (2013.01); *A61B 5/0215* (2013.01); *A61B 5/02055* (2013.01); *A61B 5/1076* (2013.01); *A61B 5/4509* (2013.01); *A61B 5/6851* (2013.01); *A61B 5/6853* (2013.01); *A61B 5/7225* (2013.01); *A61B 5/027* (2013.01); *A61B 5/036* (2013.01); *A61B 5/6852* (2013.01); *A61B 2560/0214* (2013.01); *A61B 2560/0406* (2013.01); *A61B 2560/0462* (2013.01); *A61B 2560/0468* (2013.01); *A61B 2562/02* (2013.01); *A61B 2562/0247* (2013.01); *A61B 2562/0271* (2013.01); *A61B 2562/046* (2013.01); *A61B 2562/06* (2013.01); *A61B 2562/166* (2013.01); *A61B 2562/222* (2013.01)

(56) References Cited

U.S. PATENT DOCUMENTS

| | | |
|---|---|---|
| 2010/0042010 A1 | 2/2010 | Dekker et al. |
| 2012/0053441 A1 | 3/2012 | Kassab |
| 2012/0143078 A1 | 6/2012 | Kassab et al. |
| 2013/0103124 A1 | 4/2013 | Imran |
| 2013/0204111 A1 | 8/2013 | Flanders |
| 2013/0237864 A1 | 9/2013 | Mazar et al. |
| 2014/0193021 A1 | 7/2014 | Bailey |

* cited by examiner

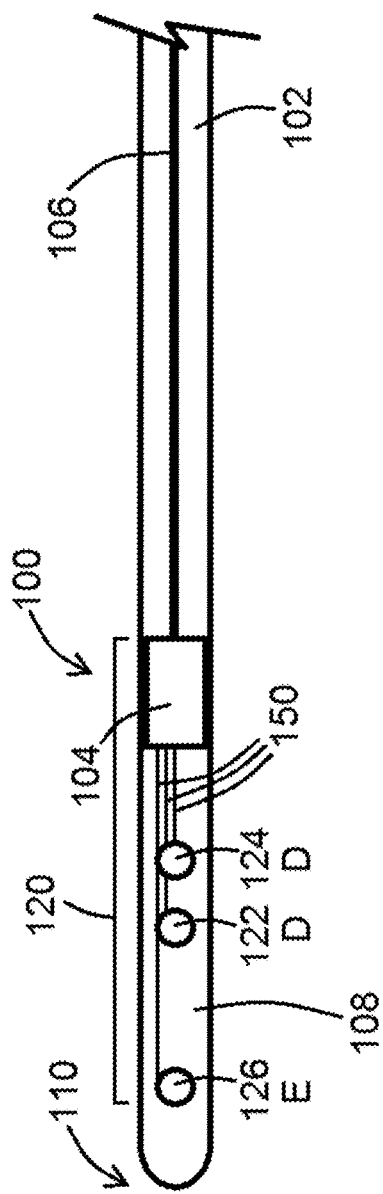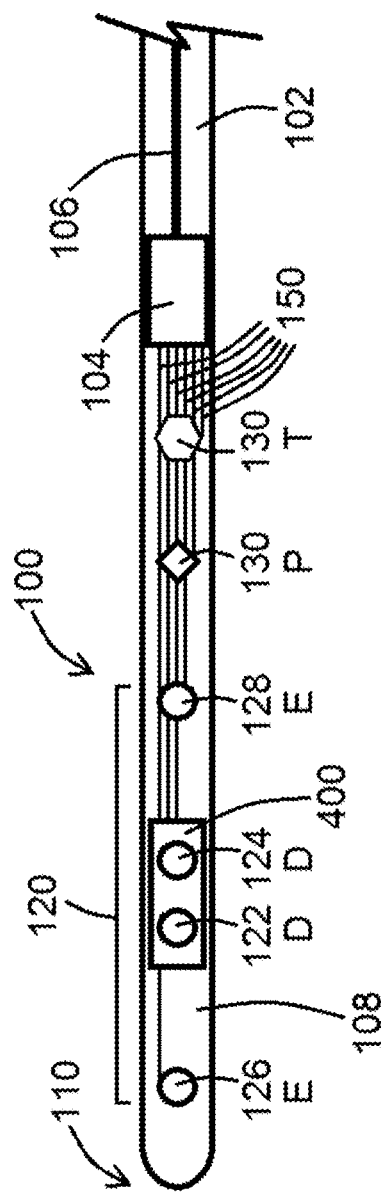

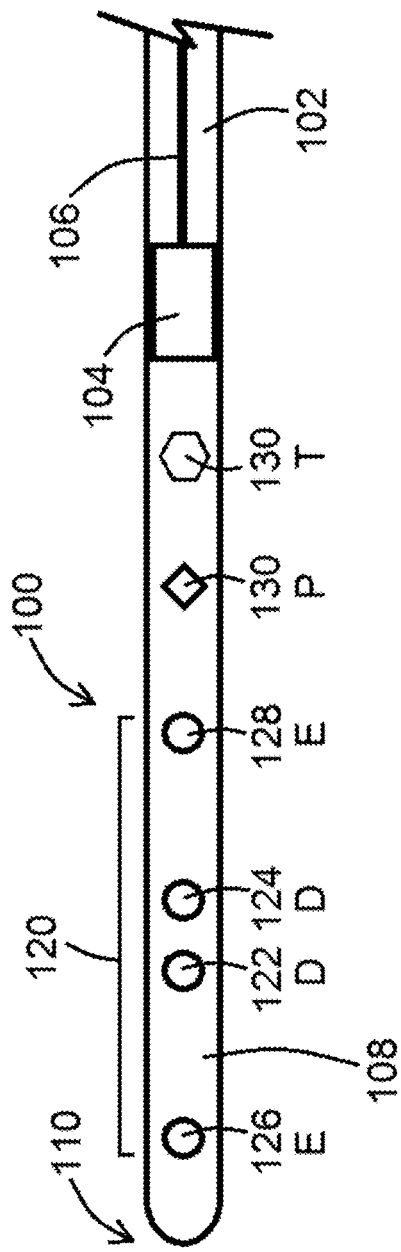
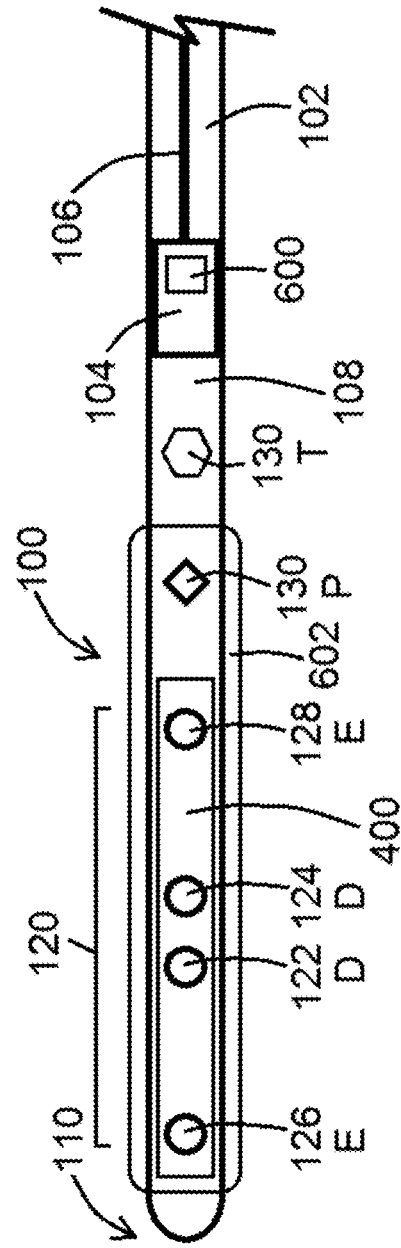

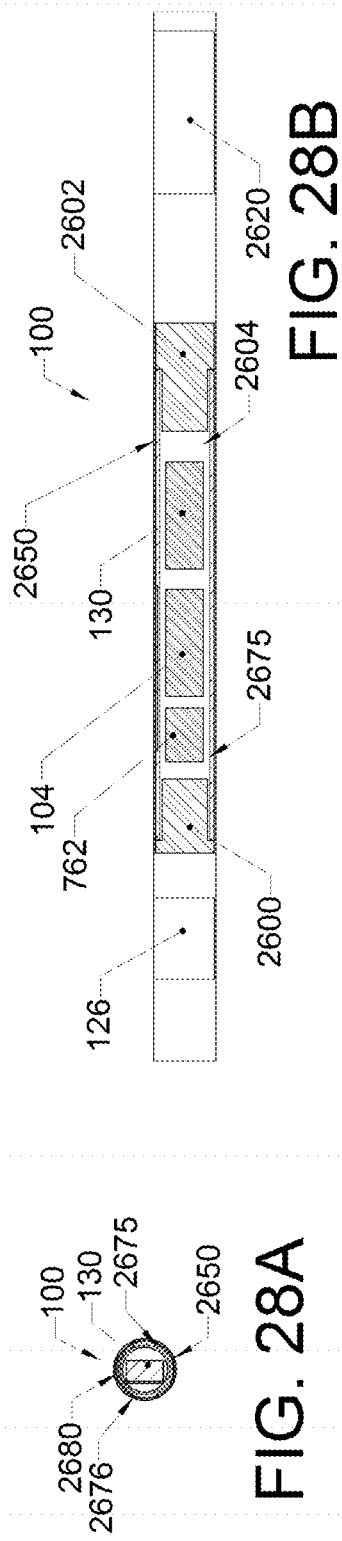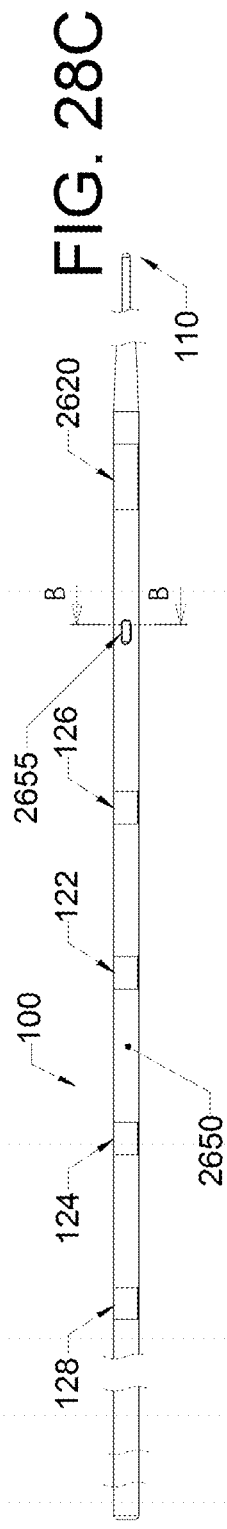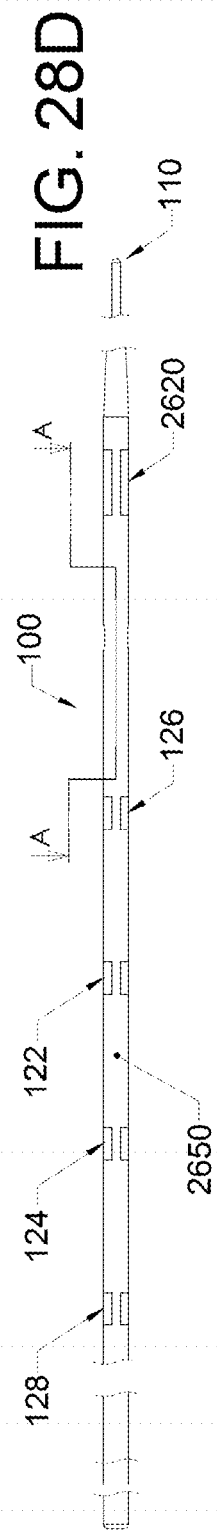

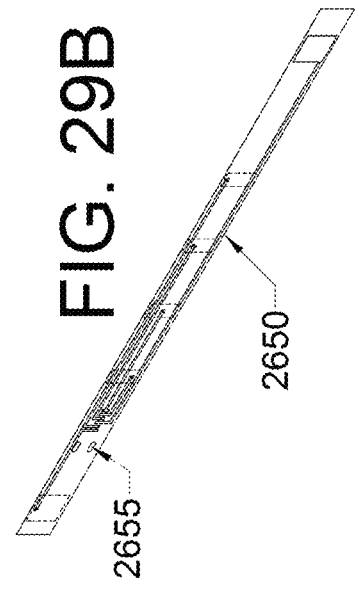
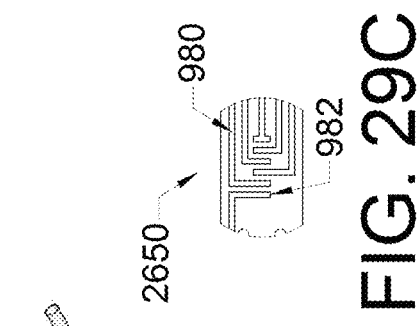
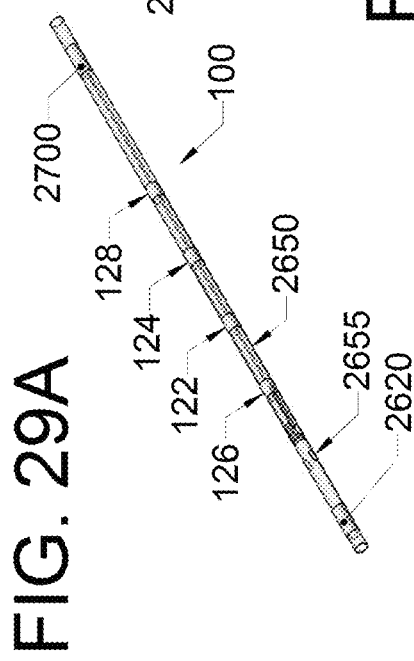
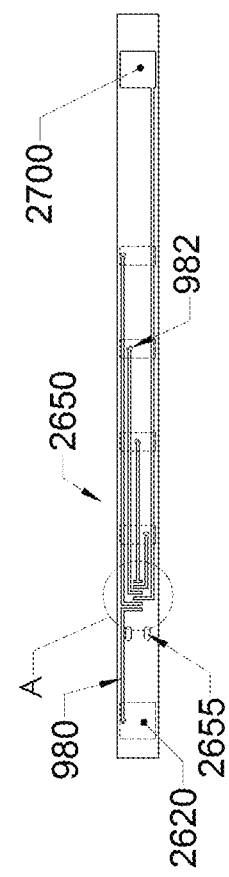
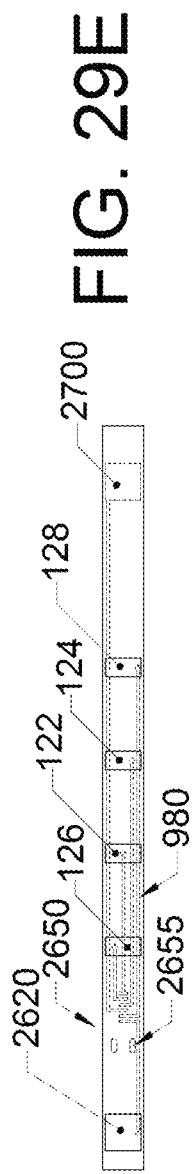

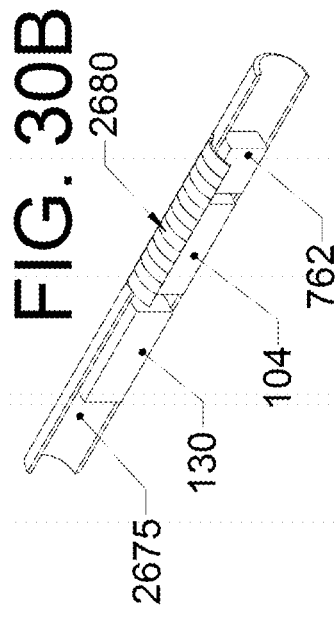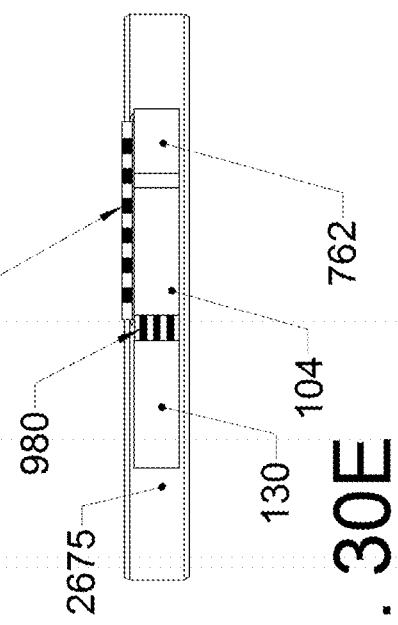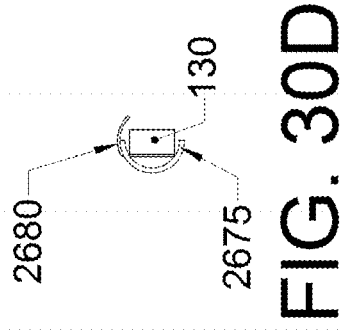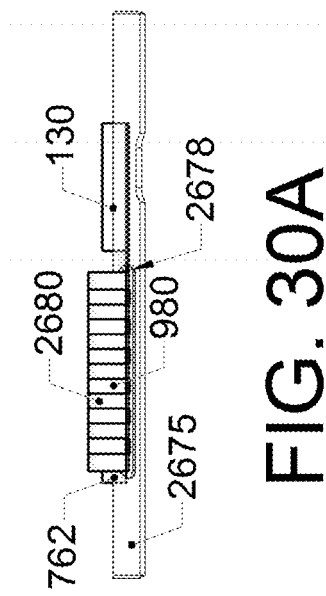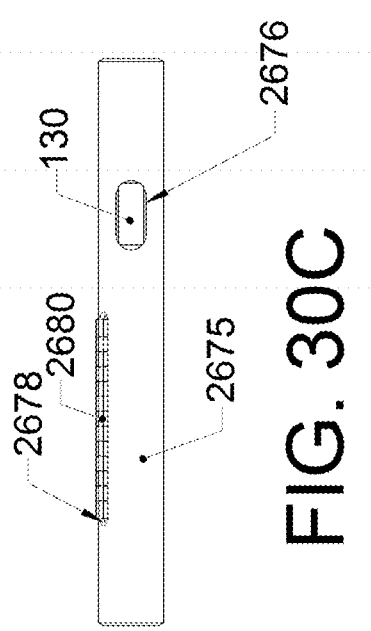

LUMINAL IMPEDANCE DEVICE WITH INTEGRATED CIRCUIT MODULES

PRIORITY

The present application is related to, claims the priority benefit of, and is a U.S. continuation patent application of, U.S. patent application Ser. No. 15/115,586, filed Jul. 29, 2016 and issued as U.S. Pat. No. 10,463,274 on Nov. 5, 2019, which is related to, claims the priority benefit of, and is U.S. 35 U.S.C. 371 national stage patent application of, International Patent Application Serial No. PCT/US15/13939, filed Jan. 30, 2015, which is related to, and claims the priority benefit of, U.S. Provisional Patent Application Ser. No. 61/933,803, filed Jan. 30, 2014. The contents of each of these applications are hereby incorporated by reference in their entirety into this disclosure.

BACKGROUND

Impedance devices, such as impedance wires and catheters, have dimensional requirements that require such devices to not only be small enough to advance through mammalian luminal organs of various sizes, but also small enough to be used in connection with other devices (such as guide catheters). The size requirements (such as overall device diameter) generally constrain a developer of such a device when certain device functionality is desired.

Over several decades medical diagnostic and therapeutic interventional procedures have become less invasive due in part to the use of more percutaneous surgical approaches, which access the intravascular system and organs through the skin with a needle. Typically the first medical device through these needles is a guidewire. The guidewire is navigated to the location of interest by use of fluoroscopic imaging, MRI, or other imaging modalities. The guidewire, once navigated to the site of interest, becomes the access pathway for a variety of catheters needed to complete the percutaneous interventional procedure.

There exists a significant need to reduce the total cost of care for these percutaneous procedures and the diseases they are treating. Recent solutions to this need include, among other things, an increase in smart devices to quickly, accurately and intelligently diagnose and inform the interventional procedure. This solution includes adding sensors to guidewires. A clinical application such as angioplasty/stenting to open a vessel stenosis may ideally use intravascular pressure sensing to determine pressure changes in a vessel of interest and the applicability of therapy. Once a pressure gradient or fraction flow reserve is determined to be significant, a clinician may want to use intravascular sensors to more accurately size the vessel, determine location of lipid pools, determine thickness of lipid pool caps, determine force being applied to tissues, or even assess post therapy information. Ideally all of this sensor information will be derived from the guidewire as the common tool which initially accesses and remains across the site of interest.

Another solution to this reduced cost clinical need is the creation of smaller interventional devices. This includes devices for radial access, reducing hospital stays. It also includes treating problems earlier in more vascular distal locations. The need for smaller percutaneous devices includes guidewires. This is not easily done however; because often the entire guidewire cross section needs to consist of a high modulus material such as stainless steel in order to provide sufficient support for diagnostic and/or therapy delivery catheters. Coronary guidewires for instance are 0.014" in diameter and most of the guidewire length is constructed of a core which is close to 0.014" in diameter, and often these are not stiff enough in lateral bending. Also, this same maximizing of Young's modulus and diameter translates into improved torque and steerability performance, which is critically important in guidewires since it is this device that the clinician uses to guide access to the site of interest.

Adding the needed sensor conductors over the length of the guidewire can take cross-sectional area and thus reduce the lateral stiffness, torsional stiffness and torsional control of the guidewire, and therefore increase guidewire delivery time, catheter delivery time, device cost and possibly total cost of care. An example of this is the marketed pressure sensing guidewire made of hypo tubes. The hypo tube is used instead of a guidewire core with a full cross section of metal so sensor conductor wires can be run down the inside of the hypo tube core, from the proximal end of the guidewire to the distal tip of the guidewire enabling the pressure sensor. Unfortunately the use of a hypo tube for the guidewire core gives this device undesirable lateral stiffness and clinical device delivery characteristics.

Furthermore, currently contemplated guidewires using pressure sensors are generally limited to enabling the dual combination of the necessary mechanical characteristics and pressure sensing. But vessel sizing, imaging, temperature, or other sensing modalities, which may further minimize procedure cost and improve therapeutic outcomes, are not enabled, either alone or in combination.

There remains a need for a higher performance guidewire that is capable of quickly and accurately measuring multiple biological metrics while maximizing high performance mechanical characteristics. In view of the same, impedance devices, and systems incorporating the same, having desired functionality with fewer parts than would normally be required and/or having components/componentry small enough to permit desired device operation, would be well received in the marketplace and solve a number of problems facing impedance device developers.

BRIEF SUMMARY

In an exemplary embodiment of an impedance device of the present disclosure, the device comprises an elongated body configured for at least partial insertion into a mammalian luminal organ of a patient, the elongated body having a first conductor extending therethrough, a proximal electrical unit operably connected to the elongated body and configured to deliver power along the first conductor, and a sensor substrate located at or near a distal end of the elongated body, the sensor substrate comprising a circuit module operably coupled to a sizing portion and a pressure sensor that are powered directly or indirectly from the power delivered through the first conductor, the circuit module operable and/or configured to a) direct the sizing portion to obtain sizing data, b) direct the pressure sensor to obtain pressure data, and c) facilitate transmission of the sizing data and/or the pressure data to the proximal electrical unit. In at least one embodiment, the first conductor comprises a single conductor, and wherein the circuit module is operable to direct operation of the sizing portion to obtain sizing data, to direct the pressure sensor to obtain pressure data, and to facilitate transmission of the sizing data and/or the pressure data to the proximal electrical unit using the power delivered along the first conductor. In at least one embodiment, the sensor substrate has at least one of a cross-sectional area and/or a diameter corresponding to a cross-sectional area and/or a diameter of the elongated body at a first location. In at least one embodiment, the sensor substrate further comprises a capacitor configured to obtain the power from the proximal electrical unit. In at least one embodiment, the sensor substrate further comprises a distal power source, the distal power source configured to charge the capacitor.

In an exemplary embodiment of an impedance device of the present disclosure, the circuit module is powered from the power from the proximal electrical unit. In at least one embodiment, the circuit module is powered by a distal power source of the sensor substrate, the distal power source configured to power the circuit module using the power delivered through the first conductor and/or from a capacitor coupled to the distal power source that is configured to receive the power delivered through the first conductor. In at least one embodiment, the sizing portion comprises a pair of detection electrodes positioned in between a pair of excitation electrodes, the pair of excitation electrodes configured to generate an electric field detectable by the pair of detection electrodes. In at least one embodiment, the sizing portion is directly coupled to the sensor substrate. In at least one embodiment, the sizing portion is positioned upon a portion of the elongated body distal to the sensor substrate.

In an exemplary embodiment of an impedance device of the present disclosure, the sizing portion and the pressure sensor are each operably connected to a multiplexer positioned upon or within the sensor substrate. In at least one embodiment, a first amplifier is positioned between the sizing portion and the multiplexer, and wherein at least a second amplifier is positioned between the pressure sensor and the multiplexer, the first amplifier configured to amplify the sizing data and the second amplifier configured to amplify the pressure data. In at least one embodiment, the multiplexer is configured to receive sizing data from the sizing portion and pressure data from the pressure sensor and is further configured to separately transmit the sizing data and the pressure data to the circuit module. In at least one embodiment, the multiplexer is configured to receive sizing data from the sizing portion and pressure data from the pressure sensor and is further configured to first transmit the sizing data and the pressure data to an analog-to-digital converter positioned upon or within the sensor substrate for transmission to the circuit module. In at least one embodiment, the analog-to-digital converter is configured to convert the sizing data and the pressure data from analog data to digital data.

In an exemplary embodiment of an impedance device of the present disclosure, the sensor substrate facilitates transmission of the sizing data and/or the pressure data to the proximal electrical unit by way of a metallic element coupled to the sensor substrate, wherein the metallic element is configured to transmit the sizing data and/or the pressure data through tissue adjacent to the mammalian luminal organ to a pad positioned upon skin of the patient. In at least one embodiment, the metallic element comprises a distal ground coupled to the sensor substrate. In at least one embodiment, the metallic element comprises an electrode of the sizing portion. In at least one embodiment, the metallic element comprises the pressure sensor. In at least one embodiment, the metallic element comprises a transmitter coupled to or within the sensor substrate.

In an exemplary embodiment of an impedance device of the present disclosure, the device further comprises a first switch positioned between the elongated body and the circuit module. In at least one embodiment, the device further comprises a second switch positioned between a distal power source of the sensor substrate and a distal ground coupled to the sensor substrate. In at least one embodiment, power from the proximal electrical unit is delivered by a power source of the proximal electrical unit. In at least one embodiment, the elongated body further has a second conductor extending therethrough, wherein the power is delivered from the proximal electrical unit to the sensor substrate using the first conductor, and wherein the sizing data and/or the pressure data is transmitted from the sensor substrate to the proximal electrical unit using the second conductor.

In an exemplary embodiment of an impedance device of the present disclosure, the elongated body comprises a proximal segment having the first conductor extending therethrough, the proximal segment configured to connect to an inner segment. In at least one embodiment, the proximal segment is connected to the inner segment, and wherein the inner segment is configured to connect to a distal segment. In at least one embodiment, the sensor substrate is configured to fit within the inner segment.

In an exemplary embodiment of an impedance device of the present disclosure, the first conductor is positioned within a proximal segment of the elongated body, and wherein the proximal segment is connected to an inner segment which is further connected to a distal segment. In at least one embodiment, the inner segment comprises the sensor substrate. In at least one embodiment, the circuit module and the pressure sensor are configured to fit within a component housing, and wherein the component housing is configured to fit within the inner segment. In at least one embodiment, the impedance device further comprises a capacitor connected to the circuit module. In at least one embodiment, the capacitor is configured to fit within the component housing. In at least one embodiment, the impedance device further comprises a transfer circuit connected to at least one of the pressure sensor, the circuit module, and the capacitor, the transfer circuit configured to electrically connect to at least one element positioned thereto.

In an exemplary embodiment of an impedance device of the present disclosure, the device further comprises a wrap configured to wrap around at least part of the elongated body at a first location. In at least one embodiment, the sizing portion comprises a plurality of electrodes configured to obtain the sizing data, and wherein the plurality of electrodes are coupled to or formed as part of the wrap. In at least one embodiment, when the wrap is positioned around at least part of the elongated body at the first location, at least one of the plurality of electrodes is electrically coupled to the circuit module. In at least one embodiment, the first conductor is positioned within a proximal segment of the elongated body, and wherein the proximal segment is connected to an inner segment which is further connected to a distal segment. In at least one embodiment, the circuit module and the pressure sensor are configured to fit within a component housing, and wherein the component housing is configured to fit within an inner segment.

In an exemplary embodiment of an impedance device of the present disclosure, the power delivered from the proximal electrical unit is alternating current power, wherein the circuit module is further operable to rectify the alternating current to generate direct current power to operate the sizing portion and/or the pressure sensor. In at least one embodiment, the circuit module is further operable to regulate the direct current power to reduce power ripples and to provide a constant voltage supply to the sizing portion and/or the pressure sensor. In at least one embodiment, the circuit module is further operable to modulate a carrier wave used to transmit the sizing data and/or the pressure data to the proximal electrical unit. In at least one embodiment, the circuit module is further operable to detect an interruption of the power from the proximal electrical unit. In at least one embodiment, the circuit module is further operable to control operation of the sizing portion, the pressure sensor, a temperature sensor within the sensor substrate that is operable to obtain temperature data, and a capacitor within the sensor substrate that is operably coupled to a power source within the sensor substrate.

In an exemplary embodiment of an impedance device of the present disclosure, the circuit module is further operable to generate diagnostic information using the sizing data and/or the pressure data for transmission to the proximal electrical unit. In at least one embodiment, the circuit module is further operable to produce offset voltages to the sizing portion and/or the pressure sensor and to any amplifiers connected to the sizing portion and/or the pressure sensor. In at least one embodiment, the sensor substrate further comprises a power source coupled to a capacitor, a first switch connected to a ground, and a second switch connected to the first conductor, and wherein the circuit module is further operable to control operation of the first switch and/or the second switch during and after operation of the sizing portion and/or the pressure sensor. In at least one embodiment, the circuit module is further operable to control delivery of the direct current power to one or more excitation electrodes of the sizing portion. In at least one embodiment, the circuit module is further operable to control delivery of the direct current power to one or more excitation electrodes of the sizing portion.

In an exemplary embodiment of an impedance device of the present disclosure, the circuit module is further operable to control amplification of the sizing data and/or the pressure data. In at least one embodiment, the control is performed by the circuit module and one or more amplifiers connected to the sizing portion and/or the pressure sensor. In at least one embodiment, the circuit module is further operable to sample the sizing data from the sizing portion and/or the pressure data from the pressure sensor at correct instances. In at least one embodiment, the sizing data from the sizing portion and the pressure data from the pressure sensor are analog signals, and wherein the circuit module is further operable to convert the analog signals to digital signals. In at least one embodiment, the conversion is performed by the circuit module and an analog to digital converter directly or indirectly connected to the circuit module.

In an exemplary embodiment of an impedance device of the present disclosure, the circuit module is further operable to control storage of the sizing data and/or the pressure data. In at least one embodiment, the storage is performed by the circuit module and memory directly or indirectly connected to the circuit module. In at least one embodiment, the circuit module is further operable to regulate transmission of the sizing data and/or the pressure data to the proximal electrical unit. In at least one embodiment, the regulation is performed by the circuit module and a wired or wireless communication module directly or indirectly connected to the circuit module.

In an exemplary embodiment of an impedance device of the present disclosure, the circuit module is further operable to interface with one or more radio frequency components within the sensor substrate to recover the power delivered by the proximal electrical unit using radio frequency electromagnetic waves. In at least one embodiment, the circuit module is further operable to interface with one or more radio frequency components within the sensor substrate to transmit the sizing data and/or the pressure data to the proximal electrical unit using radio frequency electromagnetic waves. In at least one embodiment, the pressure sensor is further operable to obtain temperature data. In at least one embodiment, the sensor substrate further comprises a temperature sensor, and wherein the circuit module is further operable and/or configured to direct the temperature sensor to obtain temperature data and to facilitate transmission of the temperature data to the proximal electrical unit. In at least one embodiment, the elongated body and the sensor substrate each have an outer diameter of 0.014" or less.

In an exemplary embodiment of an impedance device of the present disclosure, the elongated body and the sensor substrate are configured as a guide wire. In at least one embodiment, the impedance device is configured as a guide wire. In at least one embodiment, the proximal electrical unit is configured as a handle for the elongated body. In at least one embodiment, the proximal electrical unit is configured as a computer console. In at least one embodiment, the circuit module is operable and/or configured to facilitate transmission of the sizing data and/or the pressure data to the proximal electrical unit by directing operation of a wireless communication module configured to wirelessly transmit the sizing data and/or the pressure data to the proximal electrical unit or a component coupled thereto. In at least one embodiment, the wireless communication module is configured to wireless transmit the sizing data and/or the pressure data using radio frequency signals.

In an exemplary embodiment of an impedance device of the present disclosure, the circuit module is further operable and/or configured to temporarily cease delivery of power to the sizing portion and the pressure sensor during generation of the sizing data and/or the pressure data. In at least one embodiment, the circuit module is further operable and/or configured to temporarily cease transmission of the power delivered through the first conductor to the sensor substrate during generation of the sizing data and/or the pressure data. In at least one embodiment, the impedance device is configured so that when the circuit module identifies a temporary cessation of power from the proximal electrical unit, the sizing portion operates to obtain the sizing data and the pressure sensor operates to obtain the pressure data.

In an exemplary embodiment of an impedance device of the present disclosure, a microprocessor with the proximal electrical unit regulates the delivery of power to the first conductor. In at least one embodiment, when the microprocessor temporarily ceases delivery of power to the first conductor, the sizing portion is triggered to obtain the sizing data and/or the pressure sensor is triggered to obtain the pressure data. In at least one embodiment, the circuit module is further operable and/or configured to instruct the microprocessor to temporarily cease delivery of power to the first conductor. In at least one embodiment, the circuit module is further operable and/or configured to identify the temporary cessation of delivery of power to the first conductor. In at least one embodiment, the circuit module is further operable and/or configured to direct the sizing portion to obtain the sizing data and/or the pressure sensor to obtain the pressure data after identifying the temporary cessation of delivery of power to the first conductor.

In an exemplary embodiment of an impedance device of the present disclosure, the circuit module is further operable to capture the sizing data and the pressure data prior to facilitating transmission of the sizing data and/or the pressure data to the proximal electrical unit. In at least one embodiment, the circuit module facilitates transmission of the sizing data and/or the pressure data to the proximal electrical unit during a time when power from the proximal electrical unit to the first conductor is temporarily stopped. In at least one embodiment, the circuit module is further operable and/or configured to instruct the proximal electrical unit to temporarily stop the delivery of power to the first conductor. In at least one embodiment, the circuit module is further operable and/or configured to identify that the proximal electrical unit has temporarily stopped the delivery of power to the first conductor.

In an exemplary embodiment of an impedance device of the present disclosure, the circuit module directs the sizing portion to obtain sizing data at the same time it directs the pressure sensor to obtain pressure data. In at least one embodiment, the circuit module directs the sizing portion to obtain sizing data at a separate time from when it directs the pressure sensor to obtain pressure data. In at least one embodiment, the circuit module directs the sizing portion to obtain sizing data based upon a first trigger, the first trigger selected from the group consisting of a temperature trigger from the pressure sensor and a power trigger from the proximal electrical unit. In at least one embodiment, the temperature trigger is obtained by a half-Wheatstone bridge of the pressure sensor based upon a threshold temperature detected within the mammalian luminal organ. In at least one embodiment, the temperature trigger is obtained by the pressure sensor due to a temperature change from an injected bolus of solution. In at least one embodiment, the temperature trigger is obtained by the pressure sensor due to an increase in pressure sensor temperature due to the presence of blood.

In an exemplary embodiment of an impedance device of the present disclosure, the impedance device forms part of a system, the system further comprising a pad configured for attachment to skin of the patient and further configured to receive the sizing data and/or the pressure data from the sensor substrate through tissue of the patient. In at least one embodiment, the sizing data and/or the pressure data can be transmitted to the proximal electrical unit by way of a pad wire coupled to the pad and the proximal electrical unit. In at least one embodiment, the system further comprises a data acquisition and processing system configured to receive the sizing data and/or the pressure data from the pad.

In an exemplary embodiment of an impedance device of the present disclosure, the device comprises an elongated body configured for at least partial insertion into a mammalian luminal organ of a patient, the elongated body having a single conductor extending therethrough, a proximal electrical unit operably connected to the elongated body and configured to deliver power to the single conductor; and a sensor substrate located at or near a distal end of the elongated body, the sensor substrate comprising a circuit module operably coupled to a sizing portion and a pressure sensor that are powered directly or indirectly from the power delivered through the single conductor, the circuit module operable and/or configured to a) direct the sizing portion to obtain sizing data, b) direct the pressure sensor to obtain pressure data, and c) facilitate transmission of the sizing data and/or the pressure data to the proximal electrical unit, wherein a) and b) are performed upon the circuit module identifying that power through the single conductor from the proximal electrical unit has temporarily stopped.

In at least one embodiment, the circuit module is also coupled to a temperature sensor, and wherein the circuit module is operable and/or configured to direct the temperature sensor to obtain temperature data.

In at least one embodiment, transmission of the sizing data and/or the pressure data to the proximal electrical unit is performed upon the circuit module identifying that power through the single conductor from the proximal electrical unit has temporarily stopped.

In an exemplary embodiment of an impedance device of the present disclosure, the device comprises an elongated body configured for at least partial insertion into a mammalian luminal organ of a patient, the elongated body having a first conductor extending therethrough, a proximal electrical unit operably connected to the elongated body and configured to deliver power along the first conductor, and a sensor substrate located at or near a distal end of the elongated body, the sensor substrate comprising a circuit module operably coupled to a first sensor type and a second sensor type, the circuit module operable and/or configured to a) direct the first sensor type to obtain a first data type, b) direct the second sensor type to obtain a second data type, and c) facilitate transmission of the first data type and/or the second data type to the proximal electrical unit. In at least one embodiment, the first sensor type and the second sensor type are each selected from the group consisting of a sizing sensor, a pressure sensor, a temperature sensor, a pH sensor, a flow sensor, a velocity sensor, and a thermistor, wherein the first data type and the second data type are each selected from the group consisting of sizing data from the sizing sensor, pressure data from the pressure sensor, temperature data from the pressure sensor, temperature data from the temperature sensor, pH data from the pH sensor, flow data from the flow sensor, velocity data from the velocity sensor, and temperature data from the thermistor, and wherein the first sensor type is different from the second sensor type.

In at least one embodiment, the circuit module is further operably coupled to a third sensor type, the circuit module is further operable and/or configured to obtain a third data type and to facilitate transmission of the third data type to the proximal electrical unit, the third sensor type is selected from the group consisting of a sizing sensor, a pressure sensor, a temperature sensor, a pH sensor, a flow sensor, a velocity sensor, and a thermistor, the first third data type is each selected from the group consisting of sizing data from the sizing sensor, pressure data from the pressure sensor, temperature data from the pressure sensor, temperature data from the temperature sensor, pH data from the pH sensor, flow data from the flow sensor, velocity data from the velocity sensor, and temperature data from the thermistor, and wherein the third sensor type is different from the first sensor type and the second sensor type.

In at least one embodiment of a method of the present disclosure, the method comprises the steps of inserting a portion of an impedance device into a luminal organ of a patient, the impedance device comprising an elongated body configured for at least partial insertion into the luminal organ, the elongated body having a first conductor extending therethrough, a proximal electrical unit operably connected to the elongated body and configured to deliver power through the first conductor, and a sensor substrate located at or near a distal end of the elongated body, the sensor substrate comprising a circuit module operably coupled to a sizing portion and a pressure sensor and configured to direct operation of the sizing portion to obtain sizing data and the pressure sensor to obtain pressure data and further configured to facilitate transmission of the sizing data and/or the pressure data to the proximal electrical unit by way of the elongated body, operating the impedance device to obtain the sizing data and the pressure data within the luminal organ, transmitting one of the sizing data or the pressure data to the proximal electrical unit, and if the sizing data was transmitted to the proximal electrical unit, transmitting the pressure data to the proximal electrical unit, or if the pressure data was transmitting to the proximal electrical unit, transmitting the sizing data to the proximal electrical unit. In at least one embodiment, the sizing data and/or the pressure data is transmitted to the proximal electrical unit by first transmitting the sizing data and/or the pressure data through tissue of the patient to a pad positioned upon the patient's skin, wherein the pad is operably connected to the proximal electrical unit. In at least one embodiment, the first conductor comprises at least two conductors, wherein the power is delivered from the proximal electrical unit to the sensor substrate using one of the at least two conductors, and wherein the sizing data and/or the pressure data is transmitted from the sensor substrate to the proximal electrical unit using the other of the at least two conductors. In at least one embodiment, the operating step is performed after the circuit module identifies that the proximal electrical unit has temporarily ceased delivery of the power to the first conductor.

In an exemplary embodiment of a device and/or a system of the present disclosure, the device and/or system comprises one or more of the following components, features, and/or functionalities: an elongated body, which can be a wire (insulated or non-insulated), a catheter, a hypotube, and/or another elongated body known or developed in the medical arts relating to and for use with blood vessel entry and navigation; a circuit module, which can be formed in, placed/positioned in, or placed/positioned on, part of device; a conductive element (such as a conductive wire, for example), which can be present inside of, formed within, or positioned or coupled to an outside of, elongated body, and extend from circuit module to a location proximal to circuit module, such as a data acquisition and processing system; a data acquisition and processing system configured to send a signal (data and/or power) to a circuit module and further configured to receive data from the device; a sizing portion, comprising, for example, a plurality of electrodes used to obtain cross-sectional area, diameter, and/or other measurements of luminal organ geometry; one or more detection electrodes positioned in between two excitation electrodes; a pressure sensor; a temperature sensor; another sensor (that is not a pressure or temperature sensor); one or more wires used to connect the various electrodes and/or sensors to the circuit module; a pad configured to be positioned upon and/or generally external to the patient, so that signal data can extend from the electrodes and/or sensors, through the bloodstream, to the pad, and ultimately to, for example, a data acquisition and processing system; a pad wire for connection to a pad and to a data acquisition and processing system; and/or a microarray having at least one electrode or sensor.

In an exemplary embodiment of a device and/or a system of the present disclosure, the device and/or system is operational to perform one or more of the following procedures/tasks: obtain conductance, pressure, and/or temperature data within a mammalian luminal organ; determining the size (cross-sectional area or diameter, for example) of a mammalian luminal organ; determining parallel tissue conductance within a mammalian luminal organ; navigation of said device(s) within a luminal organ; determining the location of one or more body lumen junctions within a mammalian luminal organ; determining profiles of a luminal organ; ablating a tissue within a mammalian patient; removing stenotic lesions from a vessel; determining the existence, potential type, and/or vulnerability of a plaque within a luminal organ; determining phasic cardiac cycle measurements; determining vessel compliance; determining the velocity of a fluid flowing through a mammalian luminal organ; sizing valves using impedance and balloons, such as sizing a valve annulus for percutaneous valves; detecting and/or removing contrast from mammalian luminal organs; determining fractional flow reserve; placing leads within a mammalian luminal organ; ablation of relatively small veins for Endovascular Laser Therapy (EVLT) for treatment of venous insufficiency of varicose veins and/or other cosmetic procedures; and/or navigation through a portion of a patient's urological system, such as within a ureter, to potentially identify a stenosis or a size abnormality. Various devices and/or systems of the present disclosure are configured and/or operational as referenced herein.

In an exemplary embodiment of a device of the present disclosure, the device comprises an elongated body configured for insertion into a mammalian luminal organ, at least one sensor coupled to the elongated body and configured to obtain sensor data within the mammalian luminal organ, and a circuit module coupled to the elongated body and configured to receive the sensor data from at least one of the at least one sensor. In another embodiment, the elongated body is selected from the group consisting of a wire, a catheter, and a hypotube.

In an exemplary embodiment of an impedance device of the present disclosure, the device further comprises a conductive element coupled to the circuit module and configured to transmit current to the circuit module. In another embodiment, the conductive element is further configured to transmit a signal to the circuit module. In yet another embodiment, the circuit module is configured to transmit a signal to the conductive element, the signal at least partially comprising the sensor data or a form thereof. In an additional embodiment, the conductive element is further configured to transmit a signal from the circuit module to a data acquisition and processing system.

In an exemplary embodiment of an impedance device of the present disclosure, the at least one sensor is selected from the group consisting of an excitation electrode, a detection electrode, a pressure sensor, and a temperature sensor. In an additional embodiment, the at least one sensor comprises two or more sensors (also referred to as a "sensor set"), and wherein each of the two or more sensors are selected from the group consisting of one or more excitation electrodes, one or more detection electrodes, one or more pressure sensors, and one or more temperature sensors. In yet an additional embodiment, the at least one sensor comprises a sizing portion, the sizing portion comprising at least the at least one sensor and configured to obtain luminal organ size information using impedance.

In an exemplary embodiment of an impedance device of the present disclosure, the device further comprises a wire coupled to the at least one sensor and the circuit module, the wire configured to transmit the sensor data from the at least one sensor to the circuit module. In another embodiment, the device is configured so that the sensor data can be transmitted from the at least one sensor through a portion of a bloodstream of a patient and to a pad positioned upon or generally external to the patient. In yet another embodiment, the device is configured so that the sensor data can be transmitted from the at least one sensor to the control module and through a portion of a bloodstream of a patient and to a pad positioned upon or generally external to the patient.

In an exemplary embodiment of an impedance device of the present disclosure, the device further comprises a microarray coupled to the elongated body, wherein the at least one sensor is coupled to or forms part of the microarray. In another embodiment, the device further comprises a microarray coupled to the elongated body, wherein the microarray comprises at least one additional sensor. In yet another embodiment, the sensor data can be received wirelessly by the control module.

In an exemplary embodiment of an impedance device of the present disclosure, the device further comprises a balloon coupled to the elongated body and positioned so that at least one of the at least one sensors is positioned within the balloon.

In an exemplary embodiment of a device of the present disclosure, the device comprises an elongated body configured for insertion into a mammalian luminal organ, at least one sensor coupled to the elongated body and configured to obtain sensor data within the mammalian luminal organ, a circuit module coupled to the elongated body and configured to receive the sensor data from at least one of the at least one sensor, a conductive element coupled to the circuit module and configured to transmit current to the circuit module and further configured to transmit a signal to and/or from the circuit module, and a microarray coupled to the elongated body, wherein the at least one sensor is coupled to or forms part of the microarray.

In an exemplary embodiment of a method of the present disclosure, the method comprises the steps of positioning at least part of a device within a luminal organ of a patient, the device comprising an elongated body configured for insertion into a mammalian luminal organ, at least one sensor coupled to the elongated body and configured to obtain sensor data within the mammalian luminal organ, and a circuit module coupled to the elongated body and configured to receive the sensor data from at least one of the at least one sensor, operating the at least one sensor within the luminal organ to obtain the sensor data, and operating the control module to obtain the sensor data from the at least one sensor. In another embodiment, the sensor data comprises data selected from the group consisting of conductance data, pressure data, and temperature data. In an additional embodiment, the at least one sensor comprises one or more sensors forming a sizing portion, and wherein the step of operating the control module further comprises activating at least one of the one or more sensors to generate an electric field within the mammalian luminal organ.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 3 shows a device using a circuit module as an excitation electrode, according to an exemplary embodiment of the present disclosure;

FIG. 4 shows a device having a microassembly, according to an exemplary embodiment of the present disclosure;

FIG. 5 shows a device, according to an exemplary embodiment of the present disclosure;

FIG. 6 shows a device having a microassembly, according to an exemplary embodiment of the present disclosure;

FIG. 28A shows a cross-sectional view of a portion of a device, according to an exemplary embodiment of the present disclosure;

FIG. 28B shows a cut-away view of a device with various components therein, according to an exemplary embodiment of the present disclosure;

FIGS. 28C and 28D show side views of a device, according to exemplary embodiments of the present disclosure;

FIG. 29A shows a perspective view of part of a device with a wrap thereon, according to an exemplary embodiment of the present disclosure;

FIG. 29B shows a perspective view of a wrap, according to an exemplary embodiment of the present disclosure;

FIG. 29C shows a magnified view of a wrap, according to an exemplary embodiment of the present disclosure;

FIGS. 29D and 29E show side views (or top and bottom views) of a wrap, according to exemplary embodiments of the present disclosure;

FIG. 30A shows a side cut-away view of a component housing with components therein, according to an exemplary embodiment of the present disclosure;

FIG. 30B shows a perspective view of a component housing with components therein, according to an exemplary embodiment of the present disclosure;

FIG. 30C shows a side view, and FIG. 30D shows a cross-sectional view, of a component housing with componentry therein, according to exemplary embodiments of the present disclosure;

FIG. 30E shows a cut-away view of a component housing with components therein, according to an exemplary embodiment of the present disclosure;

Figure 1:
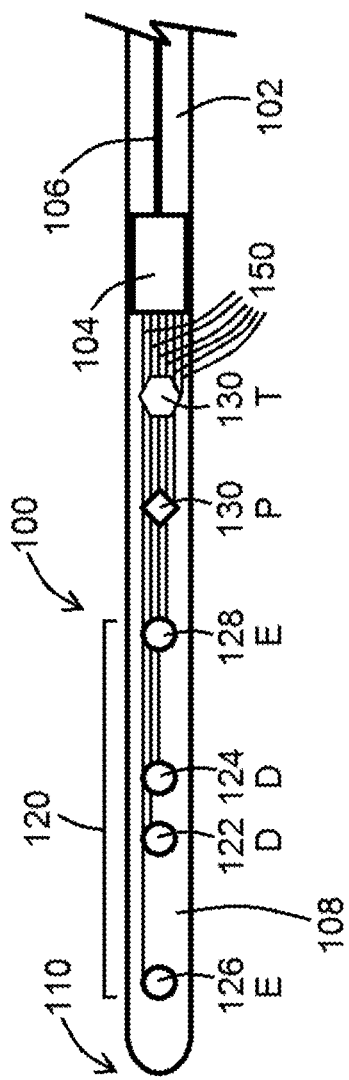
FIG. 1 shows a device, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
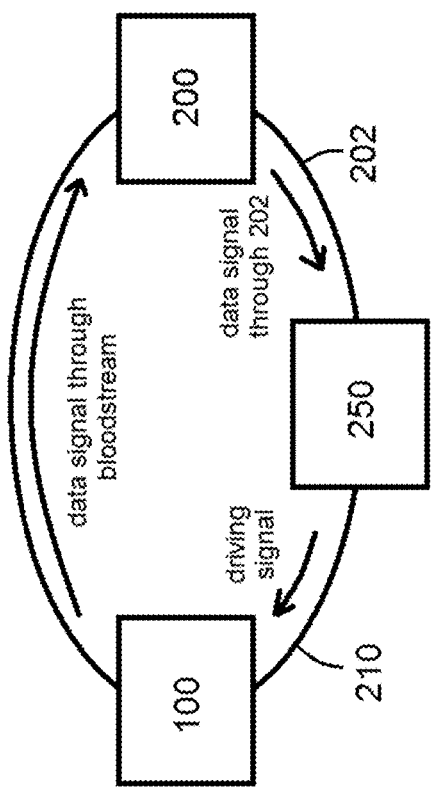
FIG. 2 shows a circuit using a device and a pad, according to an exemplary embodiment of the present disclosure.

FIG. 1 shows an exemplary distal portion of a device 100 of the present disclosure. As shown therein, device 100 comprises an elongated body 102, which can be a wire (insulated or non-insulated), a catheter, a hypotube, and/or another elongated body known or developed in the medical arts relating to and for use with blood vessel entry and navigation. A circuit module 104 (which may also be referred to herein as a control module), as shown in FIG. 1, can be formed in, placed/positioned in, or placed/positioned on, part of device 100 (which may also be referred to herein as impedance devices given their impedance operation/functionality). In embodiments of devices 100 configured as conductive wires, elongated body 102 would connect to circuit module 104 so to permit signal data to travel from elongated body 102 to circuit module 104, and in some embodiments, to allow signal data to travel from circuit module 104 to elongated body 102. In embodiments of devices 100 configured as non-conductive wires, catheters, hypotubes, or other bodies, a conductive element 106 (such as a conductive wire, for example), can be present inside of, formed within, or positioned or coupled to an outside of, elongated body 102, and extend from circuit module 104 to a location proximal to circuit module, such as a data acquisition and processing system 250 (an exemplary console, as shown in FIG. 2). In other embodiments, conductive element 106 may be formed as a coil, and use of a first conductor (such as elongated body 102) and a second conductor (such as conductive element) would allow for the transmission of power/current and the transmission of data in a bidirectional manner using only device 100.

A distal section 108 of device 100 would extend from circuit module 104 to a distal end 110 of device 100, as shown in FIG. 1. Distal section 108, in various embodiments, would include a sizing portion 120, comprising, for example, a plurality of electrodes (such as electrodes 122, 124, 126, 128 referenced in detail herein) used to obtain cross-sectional area, diameter, and/or other measurements of luminal organ geometry when device 100 is positioned within a luminal organ. Sizing portion 120, in various embodiments, may include one or more electrodes, such as, for example, two detection electrodes (122, 124, also shown as "D" in FIG. 1) positioned in between two excitation electrodes (126, 128, also shown as "E" in FIG. 1), along distal section 108 of device 100. Additional sensors or electrodes, such as a pressure sensor (an exemplary "other sensor 130" shown as "P"), and/or a temperature sensor (another exemplary "other sensor 130" shown as "T"), as shown in FIG. 1, can also be positioned along or within device 100, such as at distal section 108 or another portion of device 100. Other types of sensors 130 can be used, such as, for example, pH sensors, flow sensors, velocity sensors, thermistors, and/or other types of chemical sensors, and be included with device 100 as referenced herein with respect to pressure and/or temperature sensors 100. In addition, less than two detection electrodes 122, 124 and/or less than two excitation electrodes 126, 128 may be used to obtain sizing data, such as by using two or three overall electrodes for sizing.

Wires 150, as shown in FIG. 1, can be used to individually connect the various electrodes and/or sensors to circuit module 104. For example, and in various embodiments, one wire 150 can be used to connect excitation electrode 126 to circuit module 104, while another wire 150 can be used to connect detection electrode 122 to circuit module 104. In at least one embodiment, one connection is used to connect excitation electrode 126 to excitation electrode 128 (using one wire 150) and to then connect excitation electrode 128 to circuit module 104 (using the same wire 150 or another wire 150 connected in series), so that circuit module 104 is connected to excitation electrode 126 and 128 from one wire 150 extending from circuit module 104. Similarly, and in various embodiments, one connection is used to connect detection electrode 122 to detection electrode 124 (using one wire 150) and to then connect detection electrode 124 to circuit module 104 (using the same wire 150 or another wire 150 connected in series), so that circuit module 104 is connected to detection electrodes 122 and 124 from one wire 150 extending from circuit module 104. In such embodiments (where one connection is used to connect excitation electrodes 126, 128 and/or detection electrodes 122, 124, those pairs of electrodes would effectively act as a single electrode (as the two would be shorted together), and another electrode, such as a pad 200 (referenced in further detail below) would act as a return electrode. Such embodiments could be used for navigation (as the elements used for excitation (excitation electrodes 126, 128) and voltage recording (detection electrodes 122, 124) would be "unipolar" to the body surface), while the traditional tetrapolar embodiments (having electrodes 122, 124, 126, and 128 each connected to separate wires 150) could be used for sizing, as referenced herein. Excitation electrodes 126, 128 can, when in operation, excite an electric field within a mammalian luminal organ, which can be detected by detection electrodes 122, 124, so that conductance measurements can be obtained using impedance.

At least one embodiment of a device 100 of the present disclosure would include a circuit module 104 and a distal section 108 distal to circuit module, and further comprise a sizing portion 120 and at least one additional sensor 130, such as, for example, a temperature sensor and/or a pressure sensor.

So that data can be obtained from the various electrodes and/or sensors referenced herein, a signal (through a circuit) can be transmitted either back through elongated body 102 or conductive element 106, or via a pad 200 positioned upon and/or generally external to the patient, so that signal data can extend from the electrodes and/or sensors, through the bloodstream, to pad 200, and ultimately to, for example, data acquisition and processing system 250, as shown in FIG. 2. Pad 200, in such an embodiment, would be coupled to data acquisition and processing system 250 by way of a pad wire 202, for example, so that the overall signal circuit is complete. In various embodiments, device 100 can couple directly to data acquisition and processing system 250, or can be connected to data acquisition and processing system 250 by way of an exemplary coupler 210, as shown in FIG. 2.

Using such an exemplary device 100, or an exemplary system 300 (comprising at least device 100 and at least one other item, such as a pad 200 and/or data acquisition and processing system 250, for example), data relating to sizing (vessel cross-sectional area and/or geometry) can be obtained, along with additional data, such as relating to pressure or temperature, using the various electrodes and/or sensors referenced above. This can be accomplished using the circuit referenced above, for example, and can allow device 100 to be manufactured/configured using fewer components than would otherwise be required. For example, in device 100 embodiments where conductive element 106 is not used, a signal from device 100 can be detected using pad 200 and transmitted to data acquisition and processing system 250 without requiring some sort of return wire or conductor from device 100 to data acquisition and processing system 250. Power/current can be transmitted from data acquisition and processing system 250 to operate/activate circuit module 104, to provide current to excitation electrodes 126, 128 so that they can generate an electric field within a luminal organ detectable by one or more detection electrodes 122, 124, etc. Data can then be returned back to data acquisition and processing system 250 (such as sizing, pressure, temperature, etc., data), either via pad 200 or back through device 100, as provided in further detail below.

In at least one embodiment of a device 100 of the present disclosure, device 100 is configured with electrodes used for sizing, such as one or more detection electrodes 122, 124 and one or more excitation electrodes 126, 128, and without any other electrodes or sensors. For example, an exemplary device embodiment may comprise two detection electrodes 122, 124 positioned in between two excitation electrodes 126, 128, with wires 150 connecting the individual electrodes (or pairs of electrodes, as referenced above), to circuit module 104.

In at least one embodiment of a device 100 of the present disclosure, elongated body 102 and/or conductive element 106 (if present) can be used as a return ground in addition to being used as a signal source (such as providing a signal and/or current from data acquisition and processing system 250, whereby the current is used to ultimately activate one or more excitation electrodes 126, 128, for example). In such an exemplary embodiment, for example, the circuit could be completed using device 100 alone, such as by (a) a signal from data acquisition and processing system 250 through elongated body 102 to circuit module 104 and ultimately back through elongated body 102 to data acquisition and processing system 250, (b) a signal from data acquisition and processing system 250 through elongated body 102 to circuit module 104 and ultimately back through conductive element 106 to data acquisition and processing system 250, (c) a signal from data acquisition and processing system 250 through conductive element 106 to circuit module 104 and ultimately back through elongated body 102 to data acquisition and processing system 250, and/or (d) a signal from conductive element 106 through elongated body 102 to circuit module 104 and ultimately back through conductive element 106 to data acquisition and processing system 250. This bidirectional operation/functionality would utilize a circuit module 104 that, in various embodiments, can harvest power/current, facilitate the excitation of excitation electrodes 126, 128, have amplification capability, handle alternating and direct current, and/or transmit a signal back through elongated body 102, conductive element 106, and/or through the bloodstream to be detected by pad 200. Use of conductive elements 106 to provide power to the various sensors/electrodes could be, for example, handled by (a) its use as a single conductor in device 100 and the second electrode (such as excitation electrodes 126, 128 connected to circuit module 104 ground) and connected through an electrode (pad 200, for example) on the body surface to connect back to data acquisition and processing system 250 to complete the circuit, or (b) using two conductors in the wire (two conductive elements 106 or one conductive element 106 plus a conductive elongated body 102) to connect power and ground.

Circuit modules 104 of the present disclosure could, for example, be powered with 0-3V power, which could power conductance circuitry (within circuit modules 104 and/or in connection with excitation electrodes 126, 128) and send data/signal back to data acquisition and processing system 250, and if powered with −3-0V, other sensors/circuitry, such as pressure and/or temperature sensors (referred to herein as other sensors 130) can be powered and/or pressure and/or temperature data can be transmitted back from circuit modules 104. The various operations/functionality could be facilitated by, for example, encoding which circuit to power and transmit using a control line (such as conductive element 106) or, for example, a higher voltage pulse on the power line (elongated body 102 and/or conductive element 106) to toggle between functions, or even by using different power voltages (such as 3V and 5V, for example). Furthermore, if an exemplary conductive element 106 provides power to circuit module 104, data can be sent bidirectionally in addition to power being sent from data acquisition and processing system 250 to a sensor/electrode. In at least one embodiment, a direct current (DC) power signal can be sent along with data signals.

In various device 100 embodiments of the present disclosure, more than one circuit module 104 may be used within a single device 100. For example, and in a number of device embodiments, excitation of excitation electrodes 126, 128 and conductance measurements (the voltage across detection electrodes 122, 124) may require two or more circuit modules 104, or using one circuit module 104 and a subset of features within another circuit module 104, to facilitate the same. For example, all or a subset of the required/necessary functionality of an exemplary circuit module 104 could be implemented within a circuit module 104 as a means of reducing the required number of independent conductors integrated into the device 100 body. For example, one or more of detection electrodes 122, 124 and/or excitation electrodes 126, 128 could be condensed into an additional circuit module 104 (an exemplary integrated circuit or micromachine assembly).

In at least one embodiment, circuit module 104 would itself operate as an electrode (such as one of the excitation electrodes 126, 128 or one of the detection electrodes 122, 124), thus reducing the overall need for one of the electrodes within sizing portion 120. Such an embodiment is shown in FIG. 3, where circuit module 104 is used in place of excitation electrode 128 within sizing portion 120. In other embodiments, circuit module 104 could replace another electrode.

In at least another embodiment, such as shown in FIG. 4, at least one device 100 embodiment comprises a microassembly 400 having detection electrodes 122, 124 thereon/therein, or otherwise configured so that microassembly 400 and at least another electrode would operate as detection electrodes 122, 124. Such a microassembly 400, when used with exemplary device 100 embodiments of the present disclosure, would allow for more precision with respect to a length ("L") between detection electrodes 122, 124. In various embodiments, microassemblies 400 and/or circuit modules 104 of the present disclosure are flexible or inherently flexible given their relative size/dimensions. As referenced in one or more of the patents and/or patent applications listed below, and with respect to the use of impedance devices 100 and the various electrodes of said devices, conductance data is obtained during operation of said devices 100 as generally referenced herein. The governing relation between the measured total conductance ($G_T$) and cross-sectional area (CSA) at a particular location within a luminal organ is given by the following:

$$G_T = \frac{CSA \cdot \alpha}{L} + G_p \quad \text{[Equation 1]}$$

where L is a constant determined by the distance between detection electrodes 122, 124, α is the specific electrical conductivity of the local fluid (such as blood), and $G_p$ is the parallel conductance. In view of the same, a precise L is important, and use of a microassembly 400 to specifically place electrodes 122, 124 thereon, for example, could be more accurate than otherwise placing separate electrodes along device 100. Such a microassembly 400 could also be positioned in various locations between excitation electrodes 126, 128. Various other microassembly 400 embodiments can have any number of electrodes/sensors of the present disclosure positioned thereon, as desired.

Consistent with the foregoing, exemplary devices 100 of the present disclosure could use power provided to circuit module 104 from data acquisition and processing system 250 and leverage the power to two electrodes/sensors. For example, power from circuit module 104 to a pressure sensor 130 could be leverage to provide power to an excitation electrode 128, for example, through the same wire 150 or two wires 150 connected in series. Additional efficiencies could also be had to reduce the number of electrodes or components by way of sharing power via one wire 150 or two wires 150 connected to two electrodes and/or sensors in series, or using one component (such as circuit module 104) itself as an electrode.

An additional embodiment of an exemplary device 100 of the present disclosure is shown in FIG. 5. As shown therein, device 100 is similar to device 100 shown in FIG. 1, but without wires 150 connecting circuit module 104 to the various electrodes/sensors shown therein. In such a device embodiment, the various electrodes/sensors would operate via a wireless connection (via wireless communication) with circuit module 104, which is powered, for example, using conductive element 106 or another power source in various embodiments. In use, device 100, as shown in FIG. 5, would be operable so that the various electrodes/sensors would be able to obtain information/data, as referenced herein, and circuit module 104 could obtain/access said information/data, wirelessly. FIG. 6 shows an additional embodiment, similar to FIGS. 4 and 5, whereby a microassembly 400 having electrodes/sensors thereon is also in wireless communication with circuit module 104. Various electrodes/sensors can be positioned on, etched along, or embedded within, exemplary microassemblies 400 and/or circuit modules 104 of the present disclosure. Said wireless communication, in various embodiments, can be unilateral (such as from electrodes/sensors to circuit module 104, or vice versa), or bilateral (such as between electrodes/sensors and circuit module 104). In various embodiments, circuit module 104 (or other portions of an exemplary device 100 of the present disclosure) may comprise (be configured to have), or have in addition thereto, a wireless communication module 600 configured to communicate with various electrodes/sensors of the present disclosure. Wireless communication module 600, in various embodiments, can also be powered using conductive element 106 or another power source. FIG. 6 also shows a balloon 602 positioned around at least part of device 100, so that balloon 602 can be inflated and/or deflated as desired, such as within a luminal organ, to allow for conductance and/or other measurements to be obtained within balloon 602 using impedance, as generally referenced herein. Such an embodiment would allow, for example, sizing data (cross-sectional area, for example, using the conductance measurements), pressure data, etc., within balloon 602 at various degrees of inflation.

Figure 7:
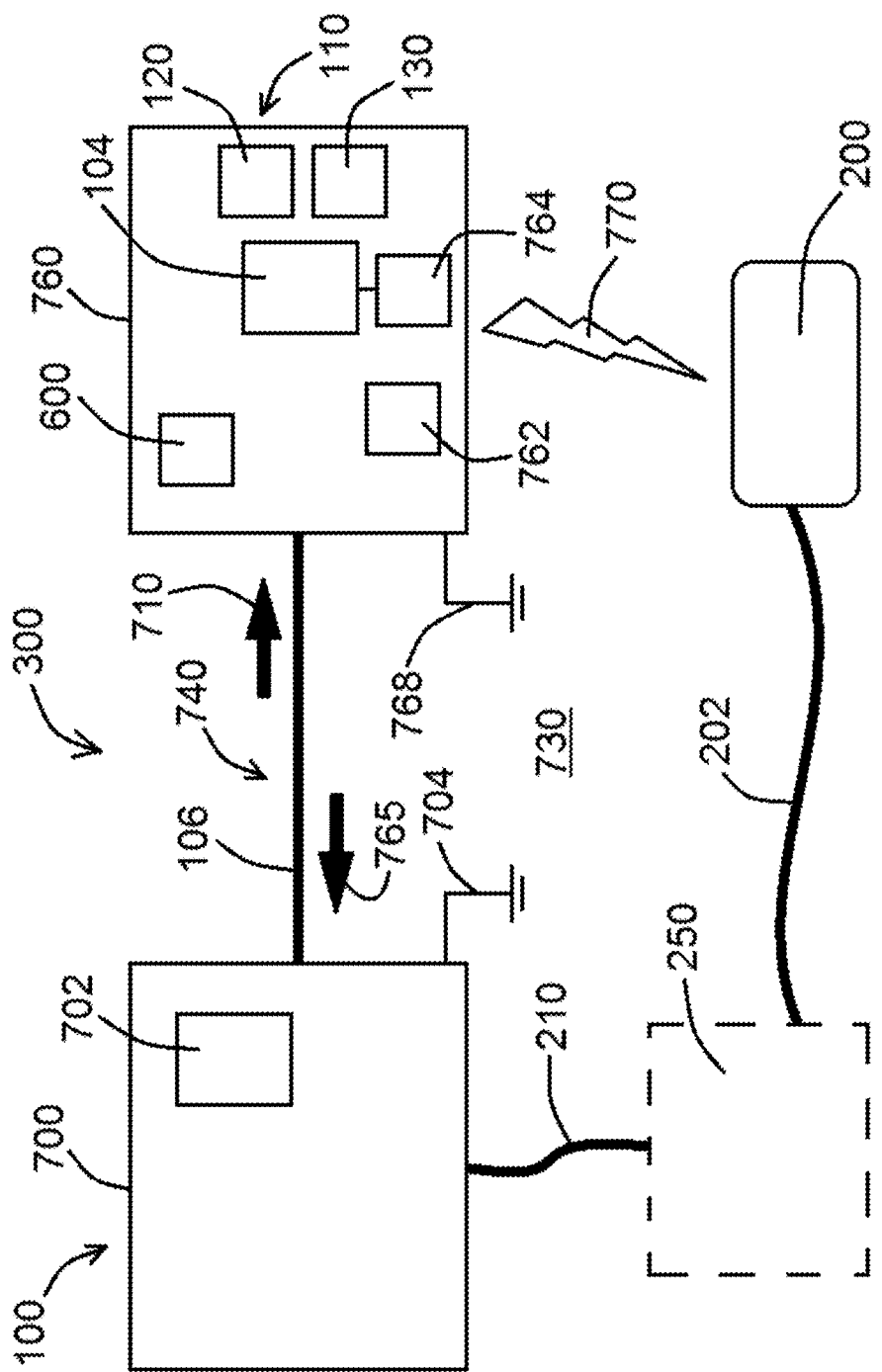
FIGS. 7, 8, and 9 show devices and systems useful to obtain data, according to exemplary embodiments of the present disclosure.
Figure 8:
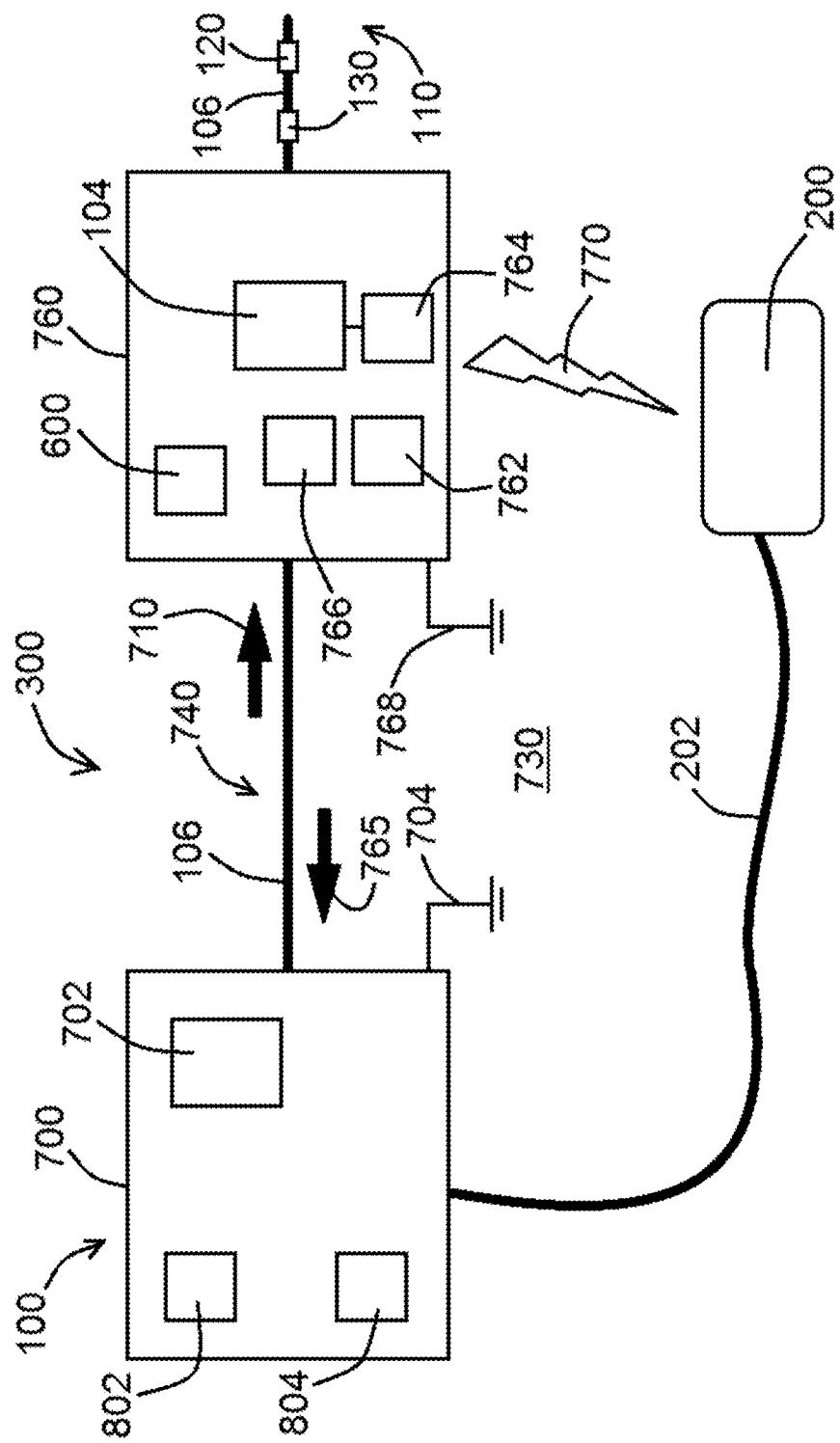

FIG. 7 shows another exemplary system 300 of the present disclosure. As shown in FIG. 7, an exemplary system 300 may comprise a device 100, which itself comprises a proximal electrical unit 700, a guide wire 740 (comprising at least one conductive element 106 therethrough (also referred to as a conductor), and sensor substrate 760 which may comprise an exemplary elongated body 102 of the present disclosure), and a sensor substrate 760 at or near a relative distal end 110 of the device 100, with said system 300 comprising one additional element, such as a pad 200 (also referred to herein as a patch electrode) and/or a data acquisition and processing system 250, for example. As shown in FIG. 7, proximal electrical unit 700 is proximal to at least part of guide wire 740, and sensor substrate 760 is distal to at least part of guide wire 740. FIG. 8 shows another exemplary system 300 embodiment, whereby device 100 has a first part of guide wire 740 between proximal electrical unit 700 and sensor substrate 760, and a second part of guide wire 740 distal to sensor substrate 760, whereby the second part of guide wire 740 has a sizing portion 120 and/or one or more other sensors 130 positioned thereon and/or embedded therein, such as a pressure sensor 130. In general, proximal electrical unit 700 can process data signals 765 (referenced in further detail herein) returning from sensor substrate 760 and generally govern operation of proximal electrical unit 700 using one or more components therein and/or coupled thereto, such as, for example, a microprocessor 900 referenced below in connection with FIG. 9. It is to be understood that the data signal 765 travels from the distal portion (sensor substrate 760) to proximal unit 700. It is further to be understood that the power signal 710 travels from the proximal unit 700 to sensor substrate 760. Transmission of both the data signal 765 and the power signal 710 is accomplished by the carrier wave 1000, referenced in further detail herein, which uses the complete electrical circuit consisting of guide wire 106, distal unit 760, distal ground 768 (or another portion of or coupled to sensor substrate 760, as referenced in further detail herein), tissue 730, pad 200, wire 202 and the proximal unit 700.

Figure 9:
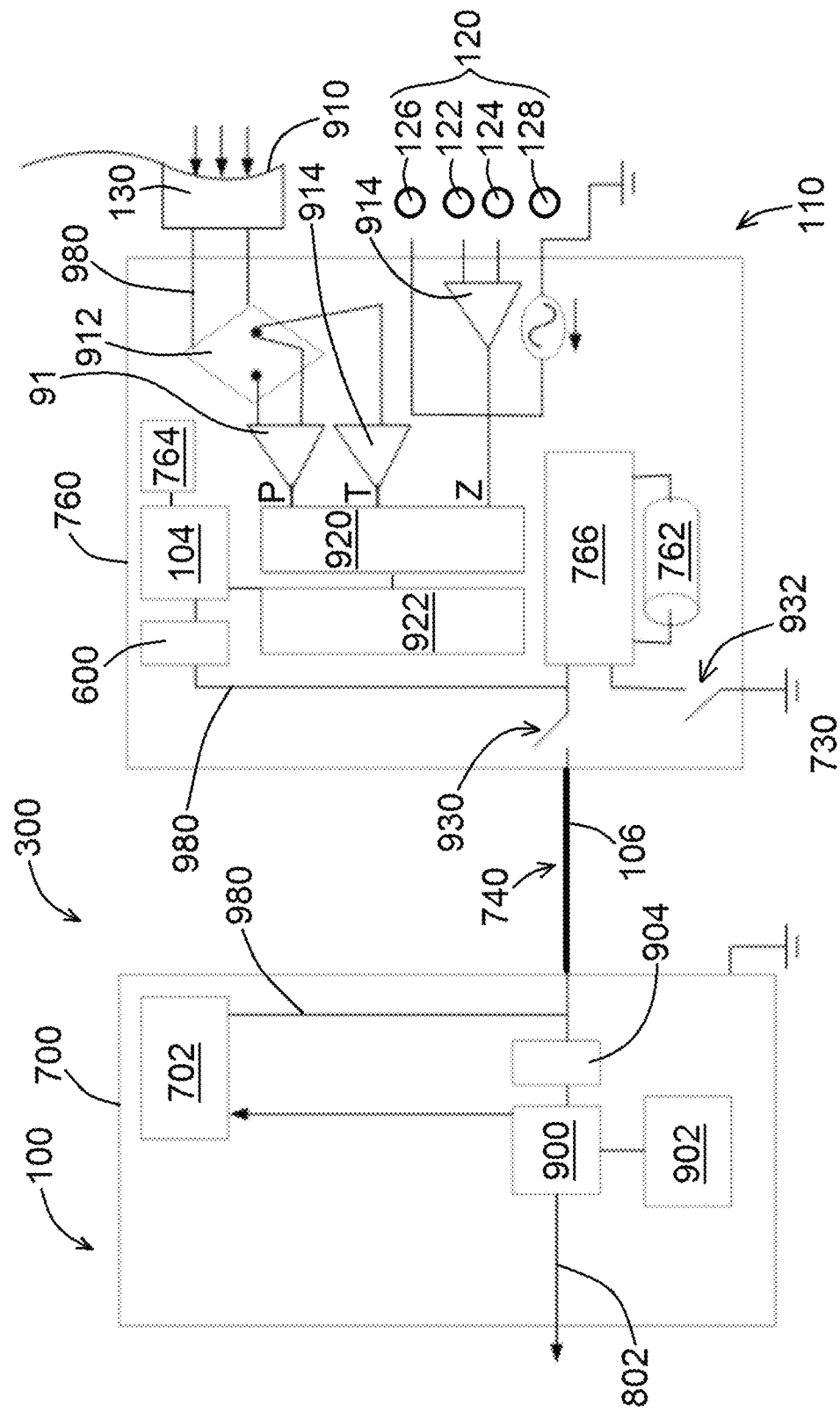

Exemplary proximal electrical units 700 of the present disclosure comprise/include at least one power source 702, which may be referred to herein as a power generator and/or a power supply. Power source 702 may comprise its own direct source of power, such as a battery embodiment of a power source 702, and/or may itself receive power from a universal serial bus (USB) or other connector 802 (as shown in FIG. 9, for example), and/or another power cable supply 804, such as a traditional electrical cord configured to be plugged into a traditional power outlet with an appropriate power regulator.

Power from power source 702, USB connector 802, and/or power cable supply 804, can be provided directly to conductor 106 and/or indirectly to conductor 106 through one of the aforementioned sources/connectors/supplies and/or one or more other components of proximal electrical unit 700. Power delivered to conductor 106 from proximal electrical unit 700 travels through conductor 106 to one or more elements/components within, upon, and/or embedded within sensor substrate 760. As shown in FIG. 7, for example, power 710 is represented by the bold arrow pointing to the right. In a preferred embodiment, power 710 is delivered from power source 702, USB connector 802, and/or power cable supply 804 as an alternating current (AC) or an oscillating direct current (DC), such as, for example, a carrier wave traveling from the proximal unit 700 to distal unit (sensor substrate 760) in the form of an alternating current at 200 KHz (alternating at 200,000 times per second).

Sensor substrate 760, as shown in FIGS. 7 and 8, may comprise a relatively small and/or thin substrate, whereby circuit module 104 (also referred to as an integrated circuit) is positioned thereon and/or embedded therein. Sensor substrate 760 may itself be a microassembly 400 of the present disclosure, or may be separate from microassembly 400. For example, sensor substrate 760 may comprise or include circuit module 104, and microassembly 400 may comprise or include one or more of a sizing portion 120 and/or one or more other sensors 130 thereon and/or therein. As shown in FIGS. 7, 8, and 9, memory 764 (an exemplary storage medium of the present disclosure that can be connected to circuit module 104 and/or other components of sensor substrate 760, whereby memory 964 can store data 765 (as referenced herein) until it can be transmitted to the proximal electrical unit 700, for example. In various embodiments, memory 764 can store various data as noted above, can include instructions and/or software therein to regulate/control various aspects of sensor substrate 700, such as provided in further detail herein.

Elements/components of sensor substrate 760 can be powered using power 710 from conductor 106 to achieve several results. One result, for example, can be to charge a capacitor 762 and/or provide power to a distal power source 766 (shown in FIG. 8) within or upon sensor substrate 760, so that power from capacitor 762 and/or distal power source 766 can be used to operate one or more elements within or coupled to sensor substrate 760. Another result can be to directly cause one or more of sizing portion 120 and/or other sensors 130 to operate (namely those requiring power to operate), such as to generate an electric field using excitation electrodes 122, 124 of sizing portion 120 (or to generate an electric field using other elements of sizing portion 120), for example. Yet another result can be to transmit a data signal 765 from one or more of sizing portion 120 and/or other sensors 130 back to proximal electrical unit 700 via one or more conductive elements 106 and/or wirelessly as noted below. As shown in FIG. 7, for example, data signal 765 is represented by the bold arrow pointing to the left. In other embodiments, data may be transmitted back to proximal electrical unit 700 via or more pads positioned upon the patient, such as, for example, using a wired or wireless communication module 600 (an exemplary transmitter configured to transmit data to proximal electrical unit 700, for example) within or coupled to sensor substrate 760 to transmit a data signal 765 to proximal electrical unit 700. In at least one embodiment, and as shown in FIG. 8, a distal power source 766 may be used in connection with capacitor 762 such that distal power source 766 can provide the necessary power to effectuate one or more of the foregoing, and in various embodiments, can also convert alternating current (such as provided by power source 702) to direct current so to operate one or more components of sensor substrate 760. As such, and as referenced above, power from conductor 106, capacitor 762, and/or distal power source 766 can be used to effectuate/facilitate one or more of the foregoing results. Capacitors 762, in various embodiments, can be used by distal power source 766 to power various circuitry within sensor substrate 760, especially in situations where power 710 from guide wire 740 may be inconsistent and therefore somewhat unreliable, whereby capacitor 762 and distal power source 766 work in connection with one another to deliver consistent and reliable power 710 to portions of sensor substrate 760.

Data signal 765, as referenced above, originates from componentry upon, within, and/or connected to sensor substrate 760 as shown in FIG. 7 or 8. Data signals 765, referenced in further detail below, can include pressure, temperature, and/or impedance data, and are transmitted back to proximal electrical unit 700 via guide wire 740, in various embodiments.

General circuits are also shown in FIGS. 7 and 8. As shown therein, and for various embodiments, power 710 generally travels from proximal electrical unit 700 through guide wire 740 and to componentry within, upon, and/or connected to sensor substrate 760. The power circuit is then completed through the body (such as indicated using ground 768 and/or signal 770, in various embodiments) to a pad 200 placed upon the body, which is then wired back to proximal electrical unit either directly, such as shown in FIG. 8, or indirectly, such as shown in FIG. 7. This can be facilitated using one or more components of sensor substrate 760 and/or one or more components coupled to sensor substrate 760, so that some sort of metallic element is in contact with the blood and/or tissue of the patient, such as by way of one or more electrodes 122, 124, 126, 128, one or more sensors 130, ground 768 (which can be, for example, some sort of antenna or other metallic element), and/or another metallic component of or coupled to sensor substrate 760. Data signals 765, as generally referenced herein, can flow in one form or another (also as described in further detail herein) from componentry of and/or coupled to sensor substrate 760, through or along guide wire 740 to proximal electrical unit 700. The data signal 765 circuit is then completed through the body via pad 200 via tissue 730, as shown in FIGS. 7 and 8.

It is noted that the components of system 300 shown in FIGS. 7 and 8 are not drawn to scale, as, for example, sensor substrate 760 would be configured to fit upon, wrap around, and/or be integrated into, part of conductor 106 so that conductor 106, as part of an exemplary elongated body 102 (such as a guide wire, for example), can be inserted into and navigated through part of a mammalian vasculature as generally referenced herein. For example, elongated body 102 (the overall guide wire, having or comprising conductor 106) can be anywhere between 0.010" and 0.050" in diameter, such as between 0.010" and 0.030" in diameter, including, but not limited to, diameters of 0.014" and 0.035". Guide wires 740 can be constructed using various metallic and polymeric materials, and can use one or more conductors 106 as referenced herein. Sensor substrate 760 and/or various sizing portion 120 components and/or sensors 130, would be at or close to such an overall diameter/size so to allow devices 100 and/or parts of systems 300 of the present disclosure to navigate within a vasculature and obtain data as generally referenced herein.

In view of the foregoing, and to complete the overall circuit necessary to operate such a system 300, power is transmitted from proximal electrical unit 700 through conductor 106 and into tissue 730 (such as via proximal ground 704, for example), to operate portions of system 300 to obtain data that is then transmitted from sensor substrate 760 to proximal electrical unit 700, so that proximal electrical unit 700 obtains feedback (in the form of data) from sensor substrate 760.

Exemplary systems 300 of the present disclosure may also have additional componentry such as shown in FIG. 9. As shown in FIG. 9, for example, one or more exemplary systems 300 of the present disclosure may comprise a device 100 comprising a proximal electrical unit 700, a guide wire 740, and a sensor substrate 760. Proximal electrical unit 700, as described herein in various embodiments, may comprise/be a handle or other configuration and include a power source 702 and optionally may include a USB or other connector 802 and/or a power cable supply 804 (as shown in FIG. 8). USB or other connector 802 can be used as a source of power, as previously described herein, and/or used to transmit data (such as data signal 765) outside of proximal electrical unit 700, such as via wired or wireless connection to a computer (not shown) connected to proximal electrical unit 700. A microprocessor 900, or functionally-equivalent componentry, may be present within or as part of proximal electrical unit 700, configured for several different types of operation, such as, for example, controlling power 710 and/or data signal 765 flow through portions of proximal electrical unit 700, accessing optional memory 902 (an exemplary storage medium of the present disclosure) in communication with microprocessor 900 so to control one or more aspects of device 100 such as the foregoing, and the like. FIG. 9 also shows a receiver 904, in communication with guide wire 740, which operates to receive one or more data signals 765 from guide wire 740, whereby said one or more data signals 765 can be provided/displayed to a user of device 100, accessed by microprocessor 900 to control future power 710, to store said one or more data signals 765 within memory 902, and/or to compare the one or more data signals 765 to each other, to other data signals 765 within memory 902, and/or to other data stored within memory 902, such as calibration information/data in connection with various sensor(s) 130 and/or sizing portion(s) 120. Data signals 765 and/or other data can be stored within memory 902 and outside of proximal electrical unit 700 so that if some or all of a connection to proximal electrical unit 700 is lost during operation, such as via USB or other connector 802, device 100 can still operate using data within memory 902 accessible using microprocessor 900. Memory 902, in various embodiments, can store various data as noted above, can include instructions and/or software therein to regulate/control various aspects of proximal electrical unit 700, interface with a data acquisition and processing system 250, etc.

Proximal electrical units 700, as generally referenced herein, can form and/or be located in a relative handle portion of device 100, as referenced above, which can be held by a medical professional using said device 100. In general, proximal electrical units 700 of the present disclosure can generate a carrier wave 1000, referenced herein in further detail and shown in FIG. 10, for example), that can be sent to sensor substrate 760 over the circuit formed by guide wire 740 and tissue 130. Exemplary carrier waves 1000 can provide power 710 necessary to operate elements within sensor substrate 760, and can be modulated by sensor substrate 760 to send data signals 765, which are recovered by proximal electrical unit 700 by the demodulation of the carrier wave 1000. Carrier waves 1000 can also be interrupted, as referenced in further detail herein, to indicate to the sensor substrate 760 that it is safe to obtain measurements. Proximal electrical units 700 of the present disclosure can also relay data signals 765 obtained from sensor substrate 760 to a data acquisition and processing system 250, such as shown in FIG. 7, for further processing and/or display purposes, which can be facilitated using USB, RS-232, Wi-Fi, Bluetooth, Zigby, and/or other known or developed wired and/or wireless means of transmitting data.

In various embodiments, data signals 765 are modulated when sent from the distal part of device (sensor substrate 760) through guide wire 740 to proximal electrical unit 700. In at least some embodiments, receiver 904 is configured to demodulate said data signals 765 so that the demodulated data signals 765 can be acted upon (received, processed, etc.) by microprocessor 900.

The distal part of device 100 (including sensor substrate 760) can have some or all of the componentry/features shown in FIG. 9. For example, and as shown therein, an exemplary sensor substrate 760 of the present disclosure may comprise a circuit module 104 (also referred to herein as an integrated circuit), a wired or wireless communication module 600 (an exemplary transmitter, configured to transmit data signals 765 from sensor substrate 760 to guide wire 740 so that data signals 765 can be provided to proximal electrical unit 700), a pressure sensor (an exemplary sensor 130), and a sizing portion 120 (comprising electrodes 122, 124, 126, 128, for example). Various wires or traces 980 may be present within proximal electrical unit 700 and/or sensor substrate 760, used to connect any number of components to one another for operation as generally referenced herein. Exemplary wires or traces 980 are shown in FIG. 9.

An exemplary pressure sensor (sensor 130) of the present disclosure may have a diaphragm 910 that bends in response to changes in pressure thereto. For example, the three left pointing arrows in FIG. 9 are indicative of a force against diaphragm 910 of sensor 130 whereby, for example, an outer portion of diaphragm 910 is elongated and an inner side of diaphragm 910 is compressed. An exemplary bridge 912, connected to sensor 910 directly or via one or more wires or traces 980, can measure extremely small differences between the inner and outer sides of diaphragm 910 (thereby detecting very small signals from sensor 130), and via one or more amplifiers 914 connected thereto, can share one or more data signals 765 from sensor 130 to multiplexer 920 and/or directly to a transmitter (wired or wireless communication module 600), which can then send data signals 765 to proximal electrical unit 700 through guide wire 740 and/or wirelessly (such as by using one or more wireless signals, radio frequency signals/waves, Bluetooth, etc.)

when a wireless transmitter is used. Amplifiers 914, as shown in FIG. 9, can amplify data signals 765 from bridge 912 so to increase the overall strength of data signals 765. As shown in FIG. 9, for example, bridge 912 can actually receive two pieces of data from the pressure sensor (sensor 130), with one being a difference between the inner and outer diaphragm 910 changes, relating solely to a change in pressure, and the other being a sum of said changes, which utilizes a temperature component as well (as a pressure sensor 130, for example, can compensate for temperature changes). In view of the same, amplifiers 914 can amplify both types of data signals 765 (pressure, indicated as "P" in FIG. 9, and temperature, indicated as "T" in FIG. 9). Similarly, an amplifier can amplify impedance (indicated as "Z" in FIG. 9) data signals 765 from sizing portion 120, as shown in FIG. 9, so to increase their overall strength prior to getting to a multiplexer 920.

Exemplary pressure sensor(s) 130 of the present disclosure can be placed near the distal tip/end 110 of the medical device 100 and is/are designed to measure the pressure of the blood. Although many embodiments are possible, at least one embodiment consists of a pair of strain gauges mounted on the opposite sides of a flexible substrate (the diaphragm 910 mentioned above), which bends and changes it curvature when the force applied on one side changes relative to the opposing side. When the two aforementioned straingauges are configured as a differential pair, the signal that is measured from a full or half Wheatstone bridge is proportional to the normal force that is applied on the pressure sensor 130. However, when the strain gauges are configured as resistors in series, then the signal that is produced is proportional to the temperature of the blood, as generally referenced above.

A multiplexer 920, shown in FIG. 9, can obtain data signals 765 from various inputs, such as sensor(s) 130 and/or sizing portion 120, and forward and/or process one data signal 765 at a time, as desired. For example, multiplexer 920, as shown in the figure, can obtain pressure and temperature data signals 765 from sensor 130 (configured as a pressure sensor), as well as sizing (impedance) data signals 765 from sizing portion 120. Multiplexer 920, after receiving said data signals 765, can share them one at a time, such as, for example, first sharing a data signal 765 from or relating to sizing portion 120, and then sharing a data signal 765 from or relating to sensor 130. An analog-to-digital converter 922, as shown in FIG. 9, can be connected to (in communication with) multiplexer 920, and operate to convert analog data signals 765 from sizing portion 120 and/or sensor(s) 130 to digital signals 765, which are then forwarded to circuit module 104 (such as an integrated circuit and/or microprocessor) and transmitted back to proximal electrical unit 700 via wired or wireless communication module 600 (an exemplary transmitter of the present disclosure). In various embodiments, wired or wireless communication module 600 is itself an electrode (or configured as an electrode), such as a coil, one of electrodes 122, 124, 126, or 128, or a separate electrode, so that data signals 765 can properly be transmitted back to proximal electrical unit 700.

Figure 13:
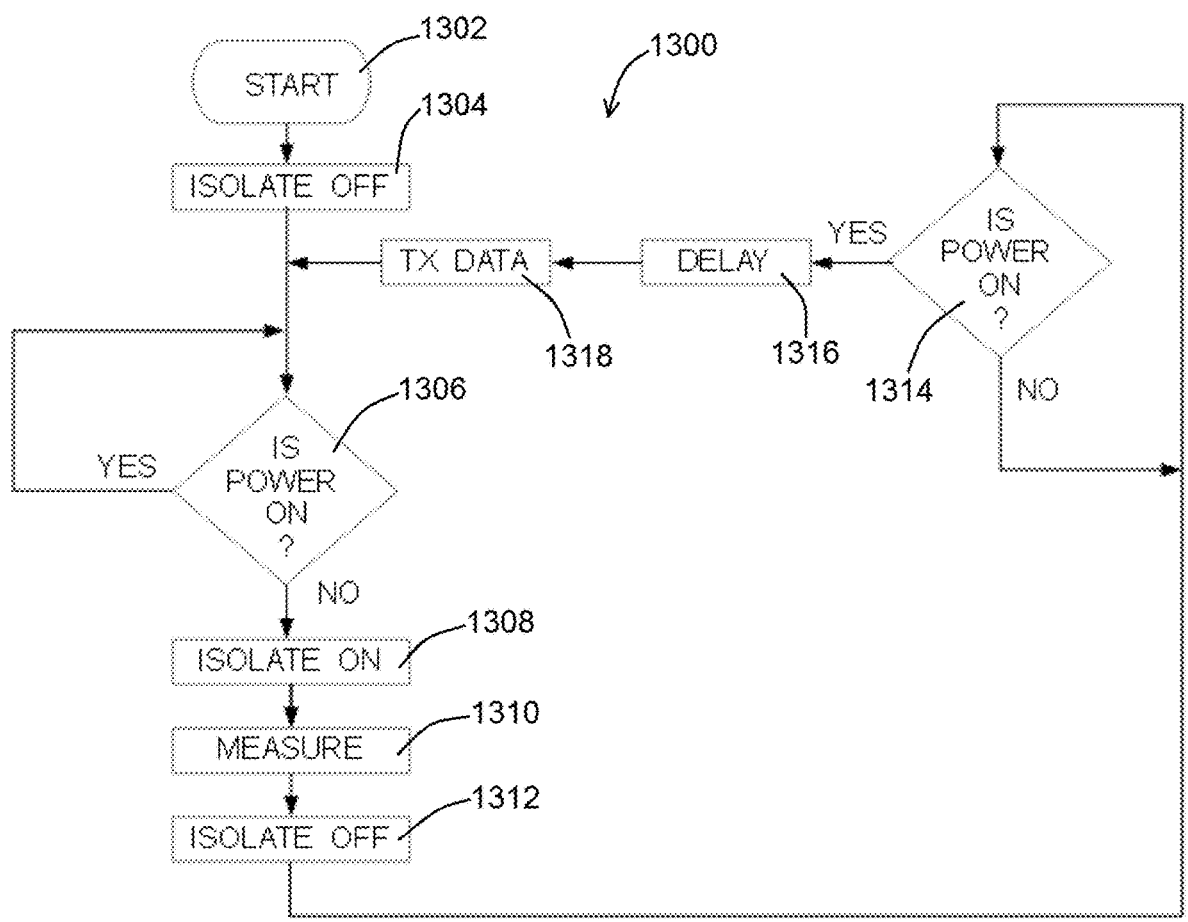
FIG. 13 shows a flowchart of events, according to an exemplary embodiment of the present disclosure.

Exemplary sensor substrates 760 may utilize one or more switches during operation. For example, a first switch 930 may be used to electrically connect (via power 710 and/or data signal(s) 765) guide wire 740, wired or wireless communication module 600, and distal power source 766. A second switch 932 may be used to electrically connect (via power 710 and/or data signal(s) 765) distal power source 766 with tissue 730, as shown in FIG. 9. FIG. 13 shows the event generation 1300 that is governed by the distal unit (sensor substrate 760), which runs as a slave to the proximal electrical unit 700. Briefly, and as shown in FIG. 13, event generation 1300 is started at start step 1302, and sensor substrate 760 is initially effectively connected to guide wire 740 and tissue 130, by being in the ISOLATE OFF state (at isolate off state 1304), which is achieved by the closure of the switches S1 (first switch 930) and S2 (second switch 932), as shown in FIG. 9. At that time, the capacitors 762 referenced herein are charged to provide the power that will be necessary to operate the distal circuitry (within sensor substrate 760) when the carrier wave 1000 will be interrupted. Distal unit (sensor substrate 760) continues to monitor the power (via is power on step 1306), and when the power is off, that is when the carrier wave 1000 is interrupted by proximal electrical unit 700, sensor substrate 760 enters into the measurement mode (measurement step 1310). First the distal tip electronics (components within sensor substrate 760) are isolated from the tissue 130, as indicated by the ISOLATE ON state in FIG. 9 (isolate on state 1308), which is achieved by the opening of the switches S1 and S2 (first switch 930 and second switch 932, respectively), as shown in FIG. 9. Subsequently, impedance, pressure and/or temperature measurements can be made, and the electrical isolation of the distal tip electronics is terminated (via isolate off state 1312). At this point, the distal tip circuitry (of sensor substrate 760) waits for the restoration of the carrier wave by the proximal circuitry (of proximal electrical unit 700) before attempting to send the resulting measurements (data signals 765) back to proximal electrical unit 700 (via data transmission step 1318), which is done by the modulation of the carrier wave 1000. Once the power is back on (via is power on step 1314), a brief delay (delay state 1316) can precede data transmission step 1318. Modulation scheme can be chosen among many that are available, such as amplitude modulation, pulse position modulation, pulse width modulation, and so on. Similarly, coding of the data (data signal 765) can be done by choosing from a large selection of techniques that are available. For example, Amplitude modulation and Manchester Coding may be preferred as they do generate signals with zero offset, which is important for data signals 765 sent over tissue 130 to prevent adverse effects and unintentional stimulation. Opening and closing of switches 930, 932 are discussed in further detail herein.

Various additional wires or traces 980 may be present within proximal electrical unit 700 and/or sensor substrate 760, used to connect any number of components to one another for operation as generally referenced herein. Exemplary wires or traces 980 are shown in FIG. 9.

Figure 10:
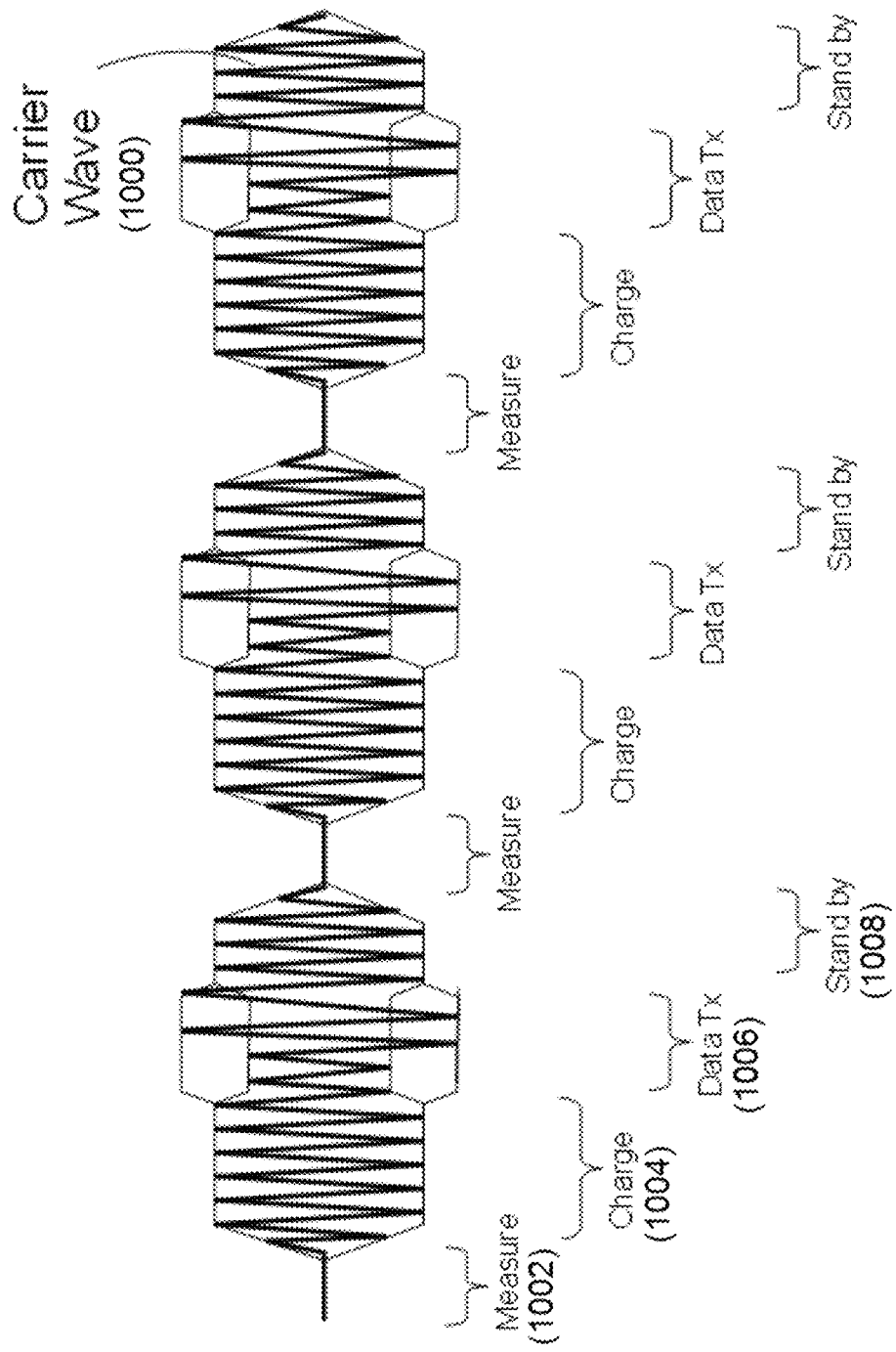
FIG. 10 shows a carrier wave and components thereof, according to an exemplary embodiment of the present disclosure.

Novel operation of exemplary devices 100 and/or systems 300 of the present disclosure can be described in view of the exemplary carrier wave timing diagram shown in FIG. 10. As shown therein, a single carrier wave 1000 is used along with the overall power signal from the proximal electrical unit to direct operation of various aspects of device 100 and/or systems 300. For example, and as shown in FIG. 10, an exemplary carrier wave 1000 has a measurement portion 1002, whereby measurements using device 100 are obtained within a mammalian vasculature, and a charge portion 1004, whereby elements within sensor substrate 760 are charged using power 710 from conductor 106 (or, phrased differently, whereby power 710 is turned back on by the proximal electrical unit 700). In measurement portion 1002, for example, components of the sensor substrate 760 identify that no power 710 is flowing thereto from guide wire 740, which can act as a trigger to obtain one or more measurements (using sensor(s) 130 and/or sizing portion(s) 120, without electrical interference due to said power 710 flow. Carrier waves 1000 of the present disclosure also include a data transmission portion 1006, whereby data obtained using device 100 is transmitted back to proximal electrical unit 700, and a stand-by portion 1008, where no data is obtained or transmitted, and which acts as a trigger for device 100 and/or system 300 to obtain additional data. During measurement portion 1002, power 710 is not provided from the proximal electrical unit 700 to the sensor substrate 760, which can act as a trigger for one or more components of sensor substrate 760 to obtain one or more pressure, temperature, and/or impedance measurements. During an exemplary data transmission portion 1006, components of the sensor substrate 760 may vary the overall amount of current/power it is draining, and proximal electrical unit 700 can monitor said power drain. Sensor substrate 760 can intentionally alter an amount of power it is draining (such as relatively less power or relatively more power, considered as a binary 0 or 1). During stand-by portion 1008, power 710 can be used to charge capacitor 762 as well, in various embodiments.

In general, and as referenced herein, exemplary devices 100 of the present disclosure are operable and/or configured to send power 710 and multiple data signals 765 over the same guide wire 740. Sizing portion 120 and/or sensor(s) 130 of the present application interface electrically, as various devices 100 and send current (power 710) and obtain various measurements (resulting in data signals 765) at the same time or very close in time to one another. Using a single core (a signal conductive element 106 or conductor), power 710 and data signals 765 can be sent over the same core, with the overall power and data circuits completed by the body (tissue 130). In view of the same, devices 100 of the present disclosure can be consider as using multiple channels, in various embodiments, of data signals 765 and power 710.

Figure 11:
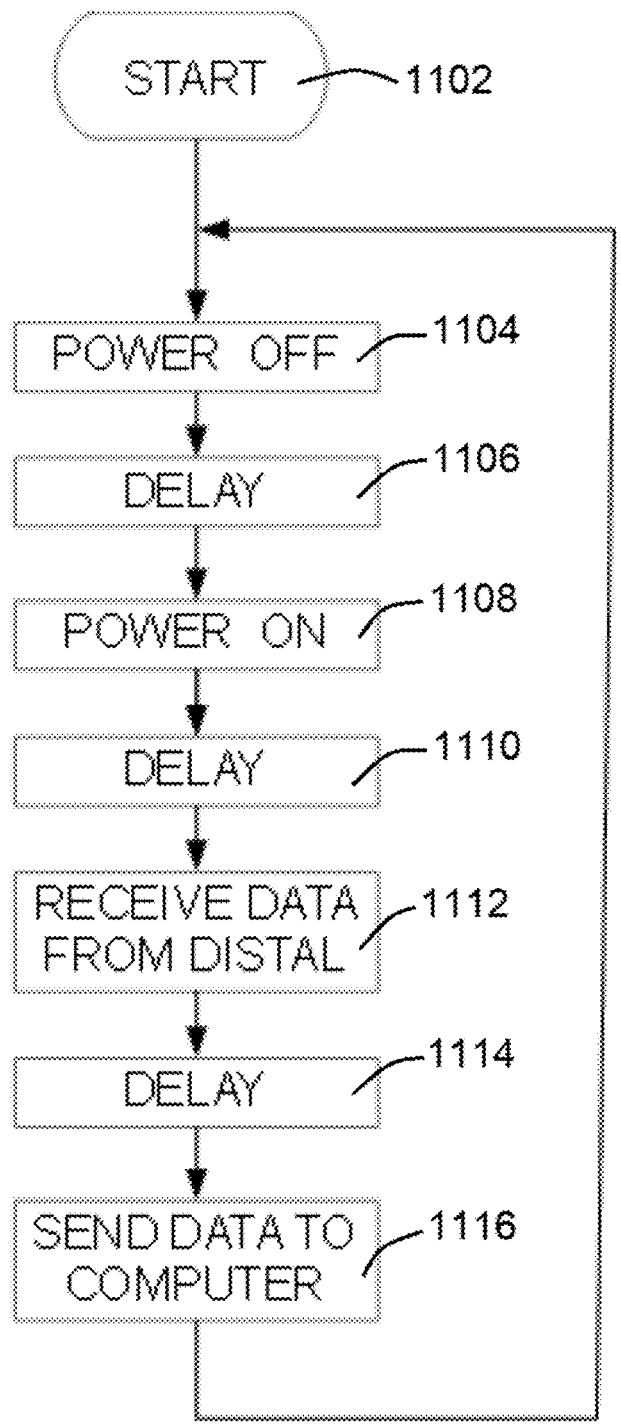
FIG. 11 shows a flowchart of events, according to an exemplary embodiment of the present disclosure.

FIG. 11 shows steps of an exemplary event generation 1100 from an exemplary proximal electrical unit 700 of the present disclosure. As shown therein, an exemplary device 100 can start operation (using start step 1102) and power transmission can be turned off (using power off step 1104), whereby measurements can be obtained using portions of device 100 and/or system 300, such as impedance, pressure, and/or temperature measurements, either at power off step 1104 or delay step 1106, which is included so to allow time for inherent tissue capacitance to go down to allow for cleaner measurements. Said measurements would be obtained when no power is being transmitted through conductor 106 to sensor substrate 760, for example, so to minimize the potential negative feedback from such a transmission during data acquisition, allowing for a cleaner (and therefore more accurate) data acquisition process. Power can then be turned on (using power on step 1108) to provide power to sensor substrate 706 so that, for example, wireless communication module 600 within sensor substrate 760 can send the data signal 765 to proximal electrical unit 700, for example. Another delay step 1110 follows the power on step 1108, so that tissue capacitance due to power on step 1108 can be reduced and allow for a cleaner transmission of data acquired using device 100 and/or system 300 within data receipt step 1112. An additional delay step 1114 may follow data receipt step 1112, with the final step in the event generation 1100 shown in FIG. 11 being to send the data signal 765 to either the proximal electrical unit 700 and/or to a data acquisition and processing system 250 at data transmission step 1116. Once the data has been transmitted at data transmission step 1116, the process can repeat itself as shown in the Figure. It is noted that delay steps 1106, 1110, and 1114 are optional, but are recommended in various embodiments so to allow for the cleanest operation of device 100 and/or system 300.

Figure 12:
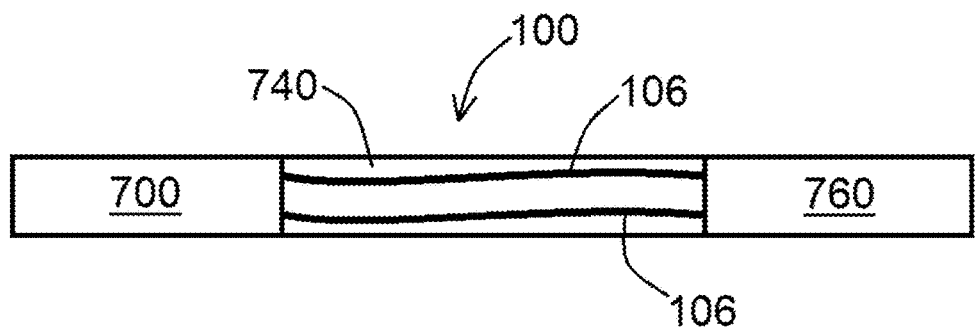
FIG. 12 shows a device having two conductive elements, according to an exemplary embodiment of the present disclosure.

Device 100 and/or system 300 embodiments using a single conductor (a single conductive element 106), as referenced herein, can use mammalian tissue 130 to complete the overall power and/or data circuits. Said devices 100 would have preferred flexibility and/or steerability, as guide wires 740 of such a small size as referenced herein would be somewhat compromised should more than one core (conductive element 106) be used. However, the present disclosure does also include disclosure of devices 100 having two or more cores (conductors/conductive elements 106), such as shown in FIG. 12, so that the overall circuit can be completed within device 100. For example, and as shown in FIG. 12, device 100 can comprise a proximal electrical unit 700, a guide wire 740 having two conductive elements 106, and a distal sensor substrate 760, each having various features and/or elements as referenced herein. Power 710 and data signals 765 (not shown in FIG. 12, but shown in other figures herein) can be transmitted over/through the loop created by proximal electrical unit 700, a first conductive element 106, sensor substrate 760, and a second conductive element 106, as shown in FIG. 12.

Figure 14:
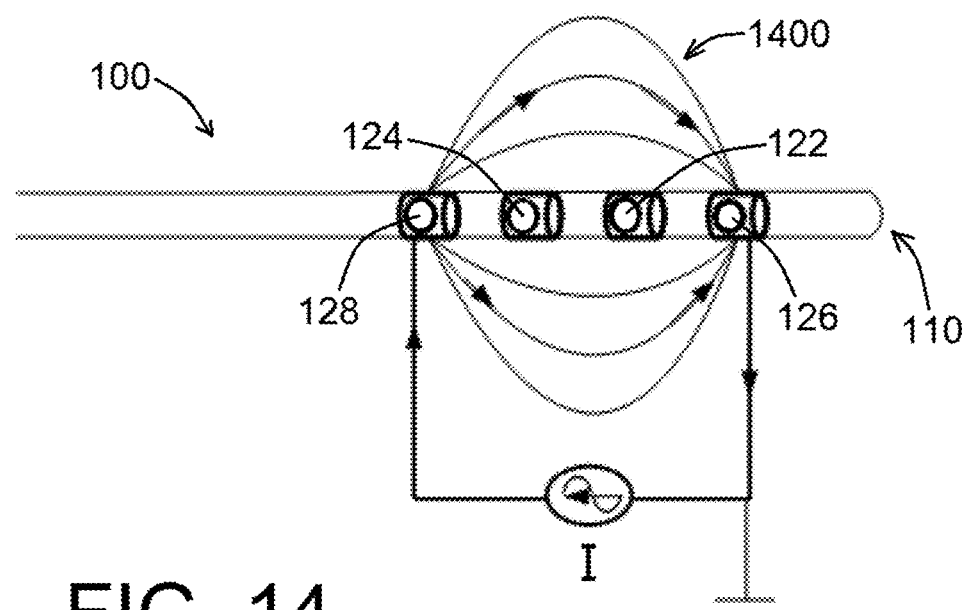
FIGS. 14, 15, 16, and 17 show operations of electrodes of exemplary devices, according to exemplary embodiments of the present disclosure.
Figure 15:
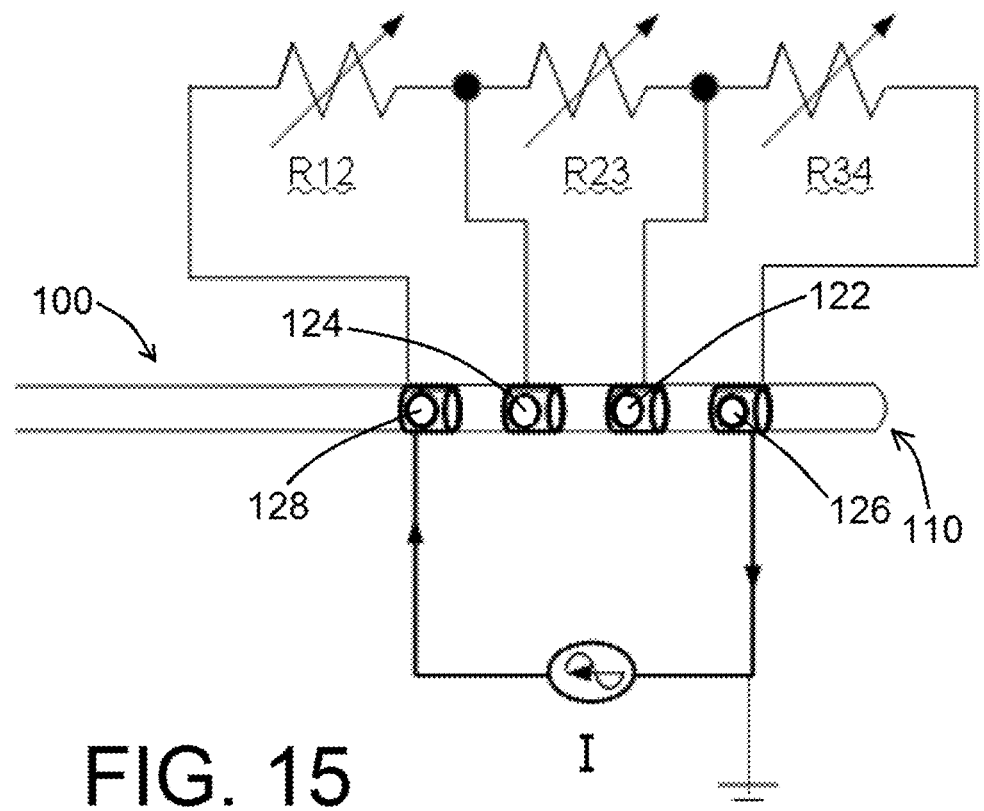
Figure 16:
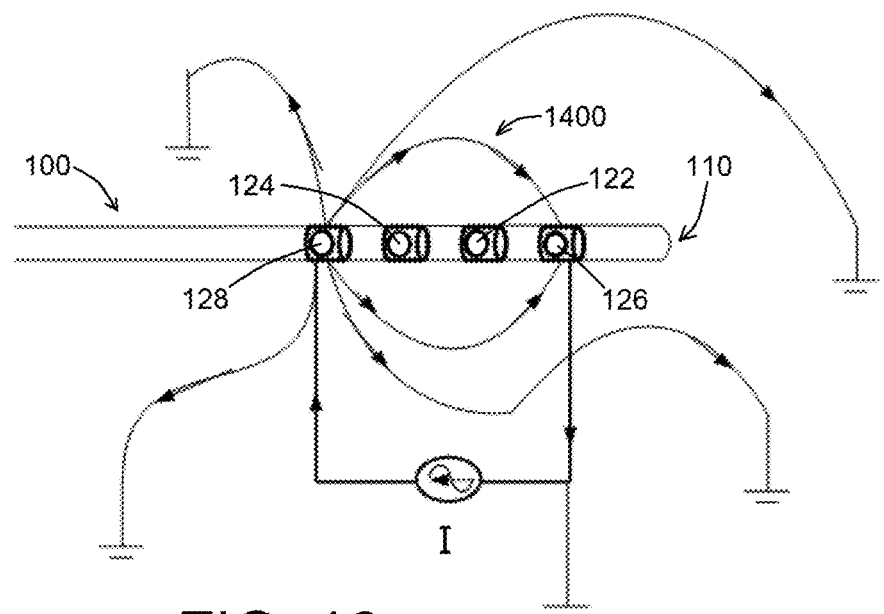
Figure 17:
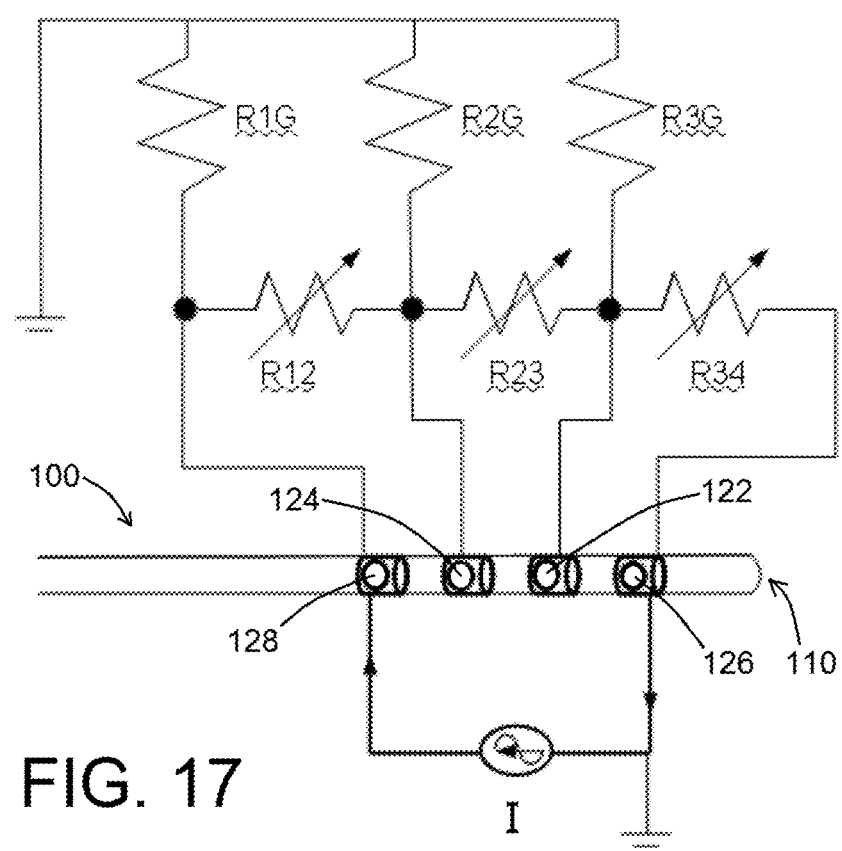

At least one issue that must be addressed by the distal circuitry (within sensor substrate 760) is the existence of a common electrical path between the power circuitry and impedance that is being measured, for example. The principles of electrical impedance measurements using the quadripolar (tetrapolar) impedance technique (two excitation electrodes 126, 128 used to generate an electric field 1400 detectable using two detection electrodes 122, 124 positioned within the two excitation electrodes 126, 128, as generally referenced herein), are illustrated in FIGS. 14 and 15. As identified within FIGS. 16 and 17, when the power is supplied over the same tissue that the impedance is measured from, a residual shunt path remains in the measurement path, making the results of the impedance measurement inaccurate. To solve this issue, measurements can be made only during the part of the cycle when the proximal circuitry (within proximal electrical unit 700) turns off the carrier wave 1000, and then the distal circuitry (within sensor substrate 760) turns on the isolation by opening first switch 930 and second switch 932 as shown in FIG. 9. In various embodiments of the present disclosure, electrodes 122, 124, 126, 128 are formed as rings around the distal portion 110 of device 100. These electrodes are usually 1 mm wide bands and are constructed from a platinum-iridium alloy, but different sizing and different materials are included within the present disclosure. Spacing between the individual electrodes 122, 124, 126, 128 is in the range of 0.5 to 10 mm.

Figure 18:
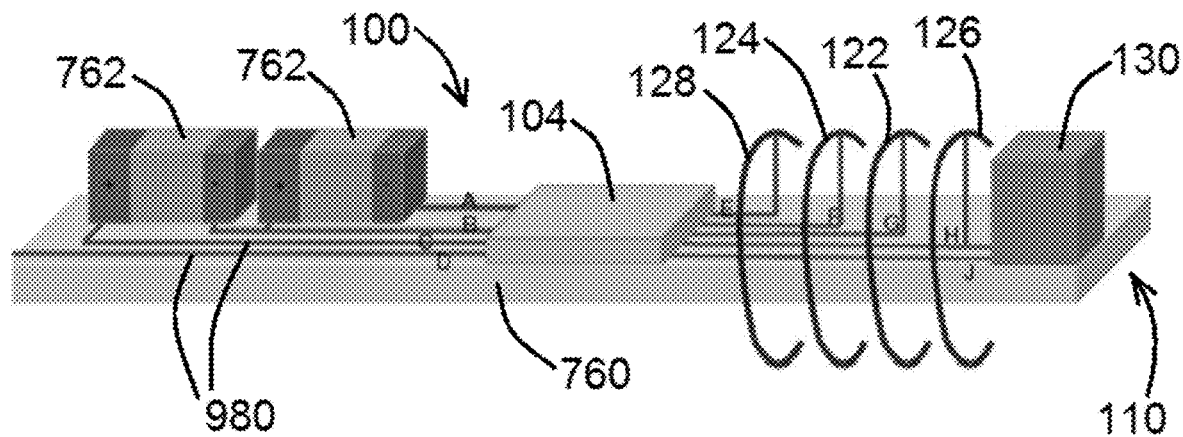
FIG. 18 shows components of a sensor substrate, according to an exemplary embodiment of the present disclosure.
Figure 19:
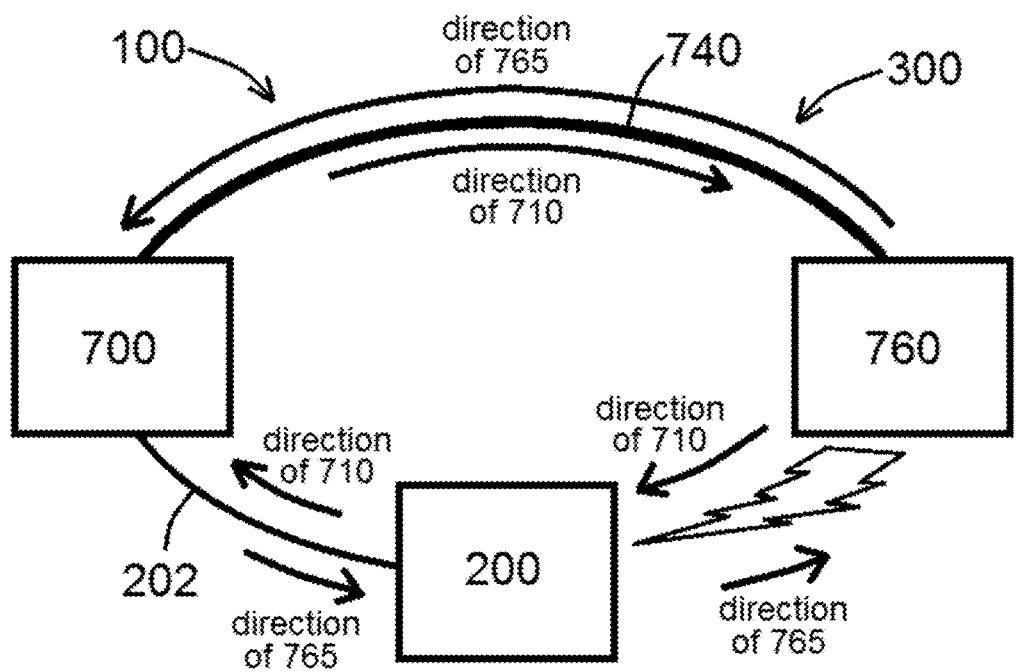
FIG. 19 shows a device and system and the directional flow of power and data signals, according to an exemplary embodiment of the present disclosure.

FIG. 18 shows a distal portion (sensor substrate 760) of an exemplary device 100 of the present disclosure, having two capacitors 762, four electrodes 122, 124, 126, 128, a pressure sensor (exemplary sensor 130), and an integrated circuit (circuit module 104), connected as shown using various wires or traces 980, configured for operation as generally referenced herein. FIG. 19 shows exemplary power 710 and data signal 765 flow directions using various devices 100 of the present disclosure, whereby, for example, power 710 flows from proximal electrical unit 700 through guide wire 740 to sensor substrate 760, to pad 200 (via one or more mechanisms or methods noted above, such as by contact of a metallic component of or coupled to sensor substrate 760 so to continue the general circuit/loop) and back to proximal electrical unit 700 via pad wire 202 and/or coupler 210, and whereby, for example, data signals 765 flow from sensor substrate 760 through guide wire 740 to proximal electrical unit 700 and back to sensor substrate 760 as shown therein to complete the loop/circuit. As shown in FIGS. 7, 8, and 19, for example, power 710 is shown as generally moving in one direction and data signals 765 are generally shown as moving in another direction. Although electrons (from oscillating alternating current (AC) or pulse direct current (DC), as desired) move in both directions along the circuit, the arrows shown in FIGS. 7, 8, and 19 are included to depict, for example, the overall flow of power 710 from power source 702 to circuit module 104 of sensor substrate 760, for example, and the overall flow of data signals 765 from circuit module 104 back to proximal electrical unit 700. With respect to power 710 and data signal flow 765, the overall circuit is completed using two conductors, at least one being one or a first conductive element 106 of guide wire 740, and the other being completed through the body back to pad 202 and pad wire 202, for example, as referenced herein.

As generally referenced herein, various devices 100 and systems 300 of the present disclosure are useful to obtain measurements within a mammalian vasculature, such as to identify locations of stenotic regions, for example, and to obtain cross-sectional area measurements using impedance to potentially aid in the pre-selection of various therapeutic devices. Impedance, blood pressure, and/or temperature can be obtained using various transvascular devices 100 and/or systems 300 of the present disclosure.

As generally referenced herein, various devices 100 of the present disclosure may comprise a sizing portion 120 having various electrodes, such as electrodes 122, 124, 126, and/or 128 referenced herein, including those four electrodes, additional electrodes, and fewer electrodes. Device 100 embodiments may comprise one or more of a sizing portion 120, a sensor 130 configured to obtain temperature measurements (such as a thermistor or thermocouple), and/or a sensor 130 configured to obtain pressure measurements (such as a pressure sensor). Other sensors 130 used in the medical arts may be incorporated into various device 100 and/or system 300 embodiments, as applicable.

EXAMPLE

Two custom circuits were built to test an exemplary embodiment of the present disclosure. One of the circuits is referred to as the proximal circuitry and performs the functions of a proximal electrical unit 700 such as shown in FIG. 7 including the generation of the carrier wave, transmission of the power, reception of the data from the distal circuitry and communication with an external computer. The operations of proximal electrical unit 700 in this example are governed by an Arduino Uno micro-controller board running a program that was written in Processing Language. This same board did communicate with an external computer using a USB connection 802. Power was obtained from a 9 Volt primary battery. The overall current draw from the battery was approximately 80 milli-Amperes.

The second circuitry is referred to as the distal circuitry and performs the functions of the elements within or upon sensor substrate 760 as shown in FIG. 7, for example, including the power recovery from the carrier wave, the data transmission by the amplitude modulation (AM) of the carrier wave using the Manchester coding, data collection using the on board sensors including the pressure sensor, temperature sensor (both exemplary sensors 130) and the quadripolar/tetrapolar impedance sensor (an exemplary sizing portion 120). The pressure that was used is a differential strain gauge sensor which also served as temperature sensor. The operation of the distal circuitry was governed by a PIC 16F690 microcontroller running a program that was written in the language C++.

Figures 20, 21:
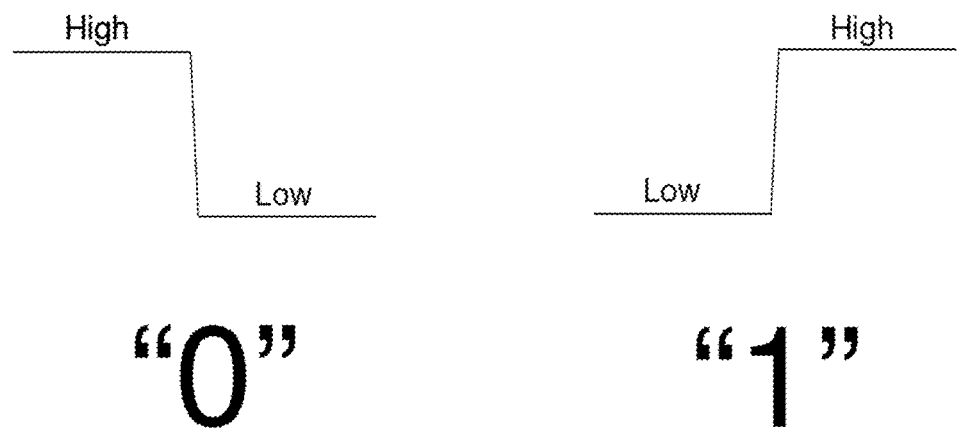
FIG. 20 shows a listing of data packages in connection with data transmission, according to an exemplary embodiment of the present disclosure.
FIG. 21 shows logic sequences of different data values, according to an exemplary embodiment of the present disclosure.

The carrier wave that is used was a 200 KHz square wave that was generated by the proximal circuitry. Data transmission was done at 9,600 baud (bits per second) using data packages that are 14 bits long, which is described below and also illustrated in FIG. 20:

Bit 01: Start Bit (Always "1")
Bit 02 & 03: Channel Number (00: Reserved, 01: Impedance, 02: Pressure, 03: Temp)
Bit 04-13: 10 bit data
Bit 14: Even Parity bit Use of Manchester code required the data transmission to be done using a logic level sequence of a low level followed by a high level for the transmission of a data value of "1" and a logic level sequence of a high level followed by a low level for the transmission of a data value of "0", as illustrated in FIG. 21.

Figure 22:
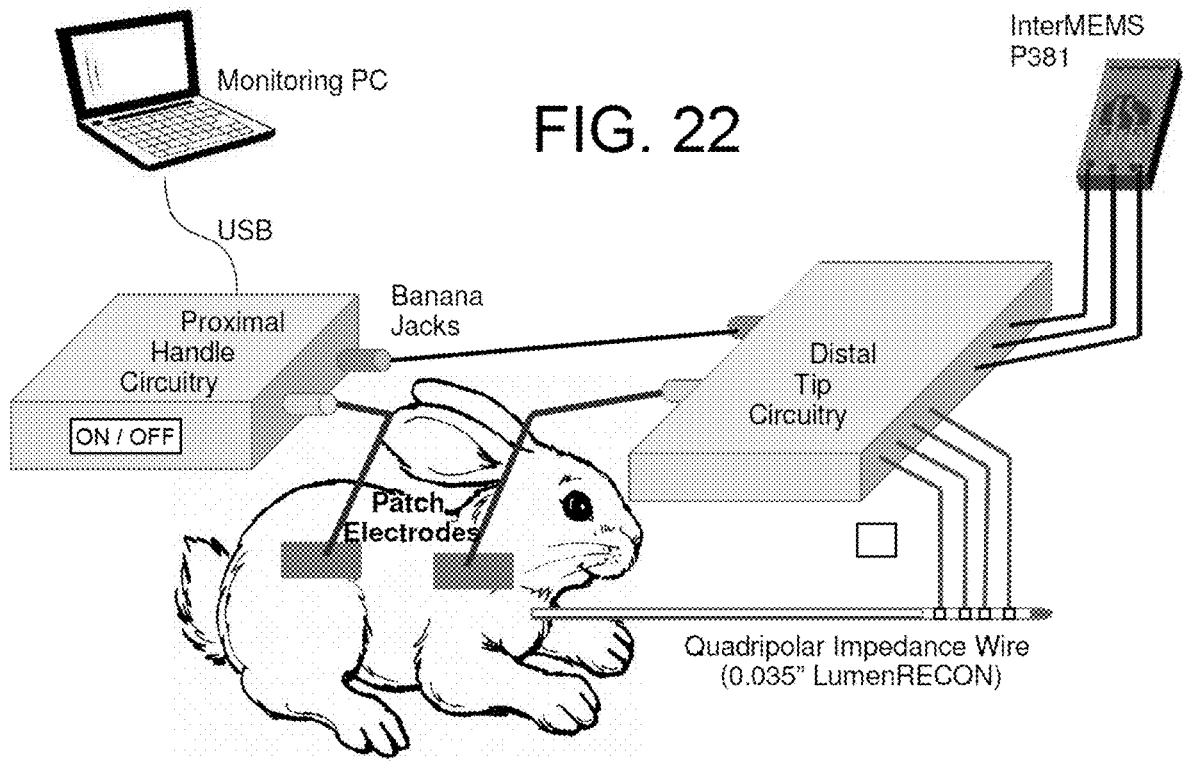
FIG. 22 shows components of a system used for a study to test the same, according to an exemplary embodiment of the present disclosure.

Electrical current intensity of the carrier wave was kept below 1 milli-Amperes at all times. The electrical circuit that is necessary to carry the wave was formed using a solid wire and the tissue as shown in FIG. 22. Connections to the tissue were made using a pair of patch electrodes.

During the acute in vivo study, a male rabbit was kept anesthetized using inhaled gas throughout the procedure. Vascular access was gained to the jugular and femoral veins via routine cut-down and with the placement of introducers at both sites. A 0.035" LumenRECON guide-wire was placed into the vein from the jugular entry point, and it was advanced into the superior vena cava. Radio-opaque dye that was introduced into the venous system was used to capture a venogram of the vessel which was later used to estimate the diameter of the vein at various locations while the guide-wire was being repositioned at four different positions. Finally, a 4 French Merit KA2 catheter was used to release room temperature normal saline (0.9% NaCl) from a distance of 19 mm from the center of the impedance electrodes numbered 2 and 3 (exemplary detection electrodes 122, 124 of an exemplary sizing portion 120).

Figure 23:
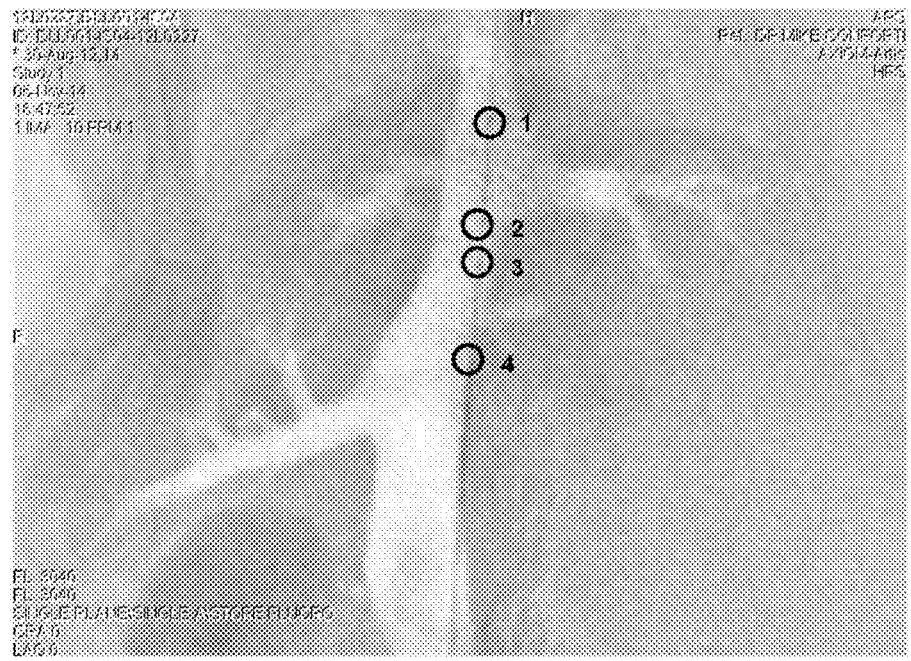
FIG. 23 shows an image of a vein of a tested animal, according to an exemplary embodiment of the present disclosure.

The following observations were made during the study:
1. When the proximal and distal circuits were connected using a solid wire+animal tissue path, the distal circuit was powered, as demonstrated by the "return signal receive indicator" that is present on the proximal circuitry.
2. When the micro-processor (an exemplary circuit module 104) residing in the distal circuitry was programmed to send fixed data values, those values were reliably received by the proximal circuitry, sent to the computer via the USB port and displayed on the computer screen, indicating that reliable data transmission over the tissue can be accomplished.
3. When the micro-processor residing in the distal circuitry was programmed to send the data from the transducers, pressure sensor data was received, and changes in the pressure data was observed when a manual force was applied to the pressure sensor, indicating that the pressure sensor interface is functional.
4. When the guide-wire is positioned at different locations in the vein of the rabbit as shown in FIG. 23, it was possible to measure the in vivo electrical impedance using the quadripolar impedance sensor (an exemplary sizing portion 120) that is on the distal circuitry. During the study, four different positions were tried, as shown in Table 1 below.

TABLE 1

Quadripolar impedance data collected during the in vivo study

| Diameter (mm) | Cross Sectional Area (mm$^2$) | $(V_2 - V_3) \times 5$ (volts) | Conductance (μ-Siemens) |
|---|---|---|---|
| 6.56 | 33.8 | 3.66 | 683.06 |
| 9.98 | 78.23 | 3.38 | 739.64 |
| 10.61 | 88.41 | 3.19 | 783.70 |
| 11.1 | 96.77 | 3.05 | 819.67 |

Figure 24:
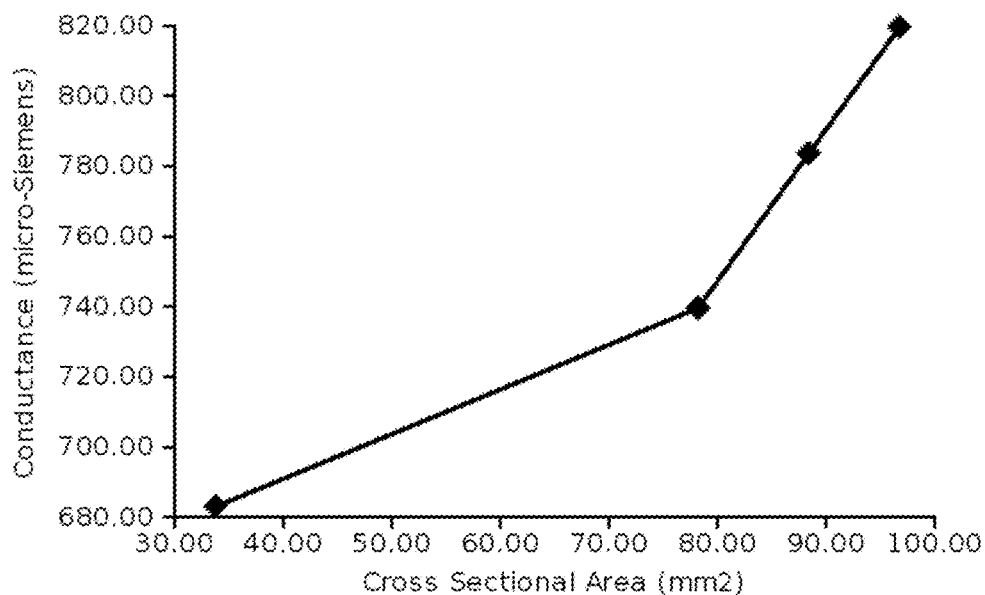
FIG. 24 shows a chart of cross sectional area relating to conductance, according to an exemplary embodiment of the present disclosure.

Data shown in tabular format in Table 1 and in graphical format in FIG. 24 show the predicted relationship between the conductance and the cross sectional area of the blood vessel.

Figure 25:
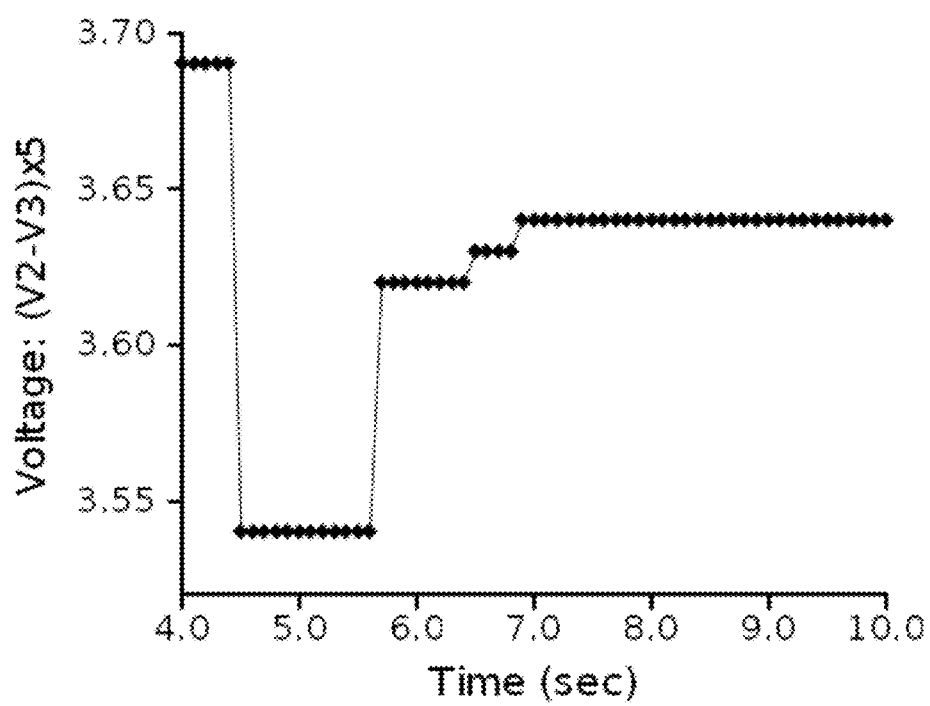
FIG. 25 shows a chart of voltage over time, according to an exemplary embodiment of the present disclosure.

When a bolus amount of normal saline (0.9% NaCl) at room temperature was injected using a 4 French Merit KA2 catheter into the vessel at a position that is 19 mm away from the center of the electrodes 2 and 3 of the guide wire, a transient response in the voltage, as shown in FIG. 25 was observed. Since normal saline has a higher conductivity compared to blood, the voltage drop observed between the electrodes 2 and 3 was reduced, as expected, during the passage of the saline over the distal portion of the catheter.

Figure 26:
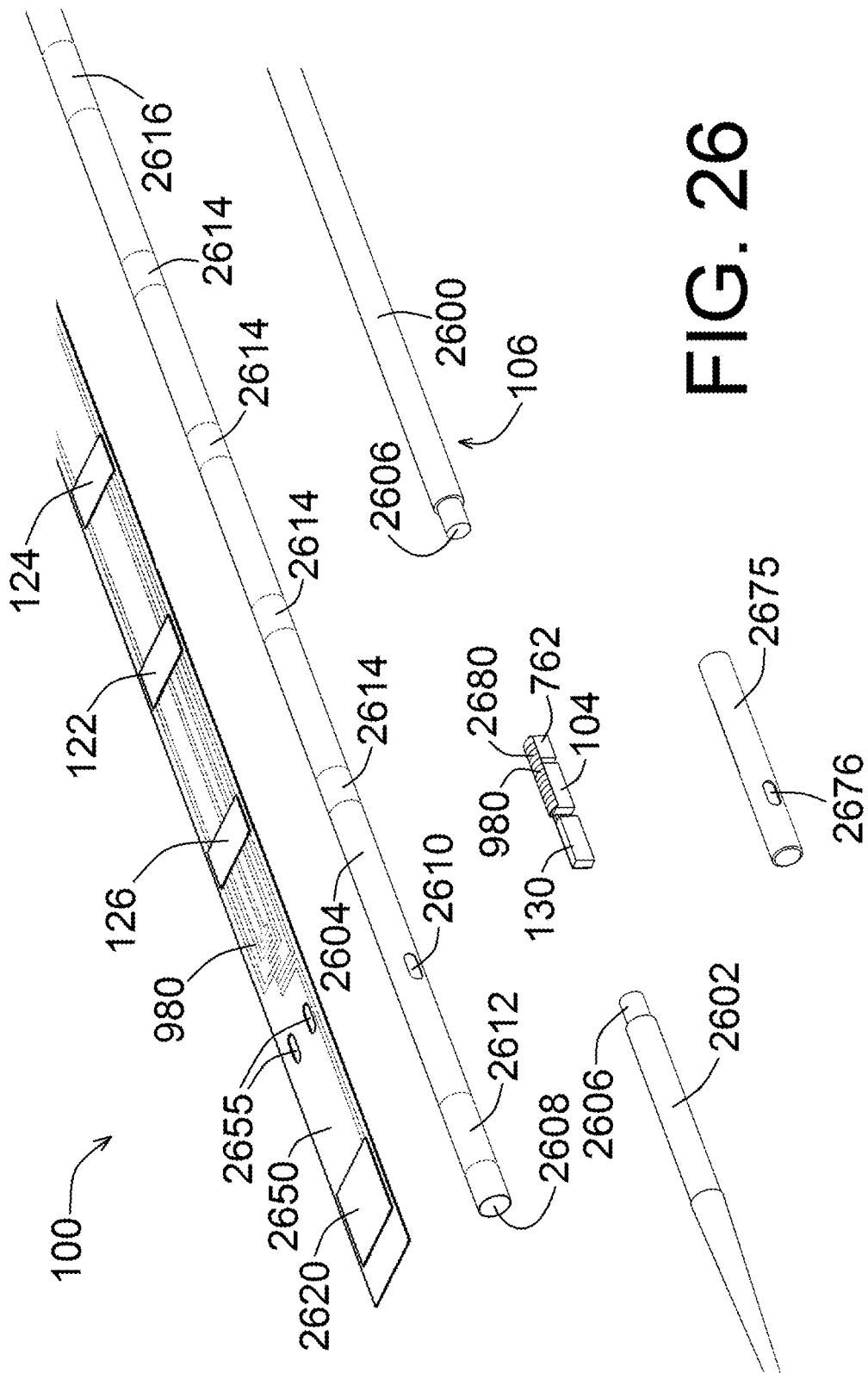
FIG. 26 shows an exploded perspective view of components of a device, according to an exemplary embodiment of the present disclosure.

Portions of an exemplary device 100 embodiment of the present disclosure are shown in the exploded component view shown in FIG. 26. As shown therein, conductive element (conductor 106) has at least three segments, namely a proximal segment 2600, a distal segment 2602, and an inner segment 2604, whereby the proximal segment 2600 and the distal segment 2602 are each configured to couple to opposite ends of inner segment 2604. Inner segment 2604, as shown in FIG. 26, is configured to receive a corresponding wrap 2650 thereon, wherein wrap 2650 is configured to be wrapped around most or all of inner segment 2604. Proximal segment 2600 can be connected/coupled to inner segment 2604, and distal segment 2602 can also be connected/coupled to inner segment 2604, using various connections and/or means, such as, for example, using one or more of an adhesive, weld (such as solder and/or using additional metal), melt (such as melting plastic), twisting, friction, etc. In at least one embodiment of a device 100 of the present disclosure, and as shown in FIG. 26, proximal segment 2600 and distal segment 2602 each have a tab 2606 at their end that will connect/couple to inner segment 2604, and inner segment 2604 has a pocket 2608 defined therein at each end to receive tabs 2606 to connect the same.

A component housing 2675, as shown in FIG. 26, is configured to receive various components of exemplary devices 100 of the present disclosure, such as a pressure sensor (an exemplary sensor 130), a circuit module 104 (also referred to herein as an integrated circuit or ASIC), and a capacitor 762. A transfer circuit 2680, as shown in FIG. 26, can comprise various wires or traces 980 that are configured to touch or engage other wires or traces 980 formed on other parts of device 100, such as on or included within wrap 2650 and/or inner segment 2604. For example, various wires or traces 980 can be used to connect one or more components within component housing 2675 and/or be used to provide the connections of transfer circuit 2680 so to allow the components within component housing 2675 to electrically communicate with other portions of device 100, such as, for example, other wires or traces 980, components of a sizing portion 120, a pressure sensor (exemplary sensor 130), conductive element (or conductor) 104, and the various parts thereof, such as proximal segment 2600 and/or distal segment 2602.

Figure 27:
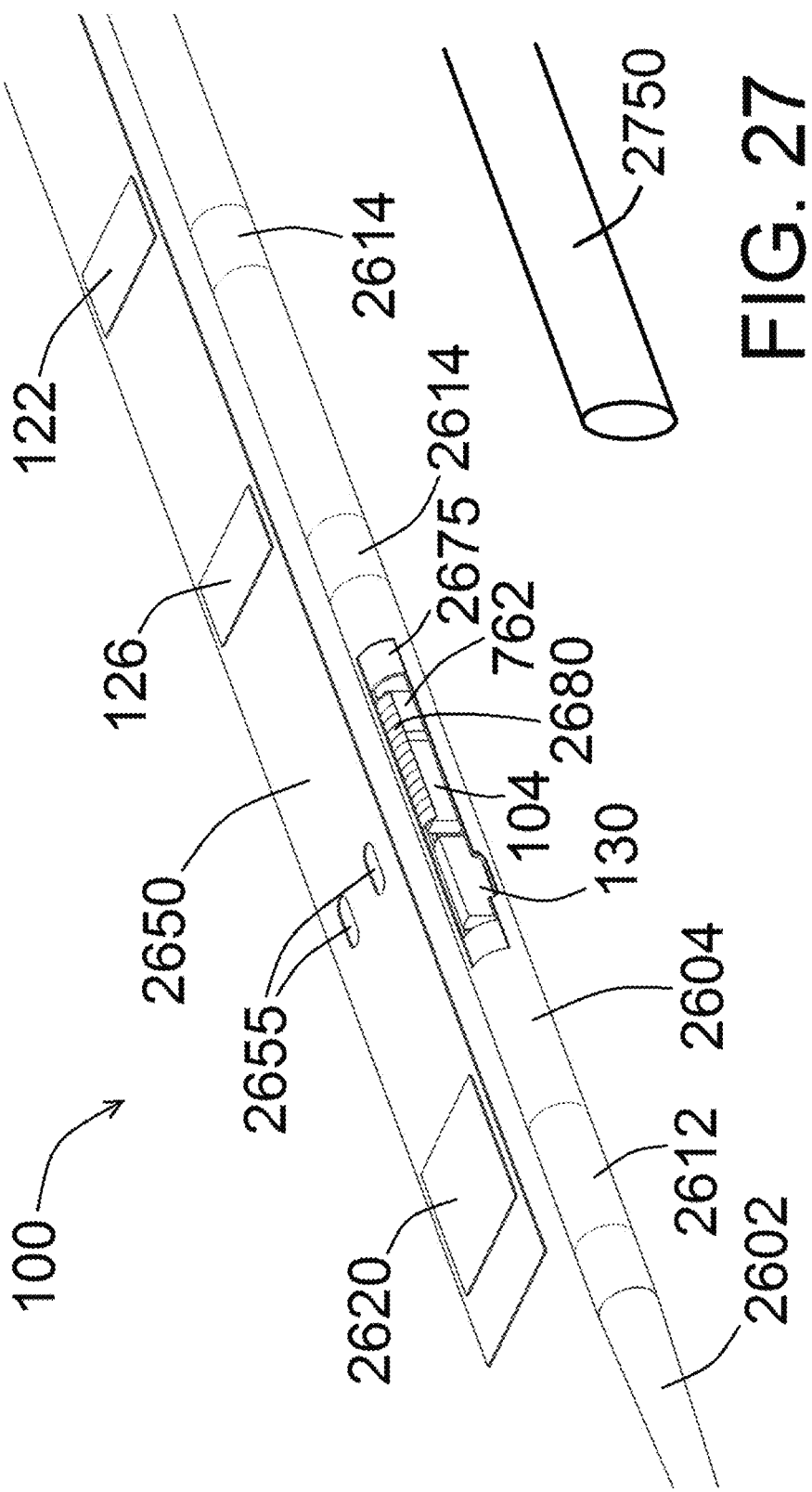
FIG. 27 shows a perspective view of elements of a device, according to an exemplary embodiment of the present disclosure.

During overall assembly of an exemplary device 100 embodiment as shown in FIGS. 26 and 27, components intended to be positioned within component housing 2675, such as the pressure sensor (sensor 130), circuit module 104, and capacitor 762, are positioned within component housing 2675. One or more component housing apertures 2676 is/are defined within component housing 2675 so to allow blood, for example, to contact pressure sensor (sensor 130) to permit pressure readings when device 100 is in use to obtain the same. Transfer circuit 2680 can either contact other wires or traces 980 of component housing 2675 that are configured to contact other wires or traces 980 or components of device 100, or transfer circuit 2680 can be exposed through a transfer circuit aperture 2678, as shown in FIGS. 30A and 30C, defined within component housing 2675 so to expose the same.

Component housing 2675, with components therein, can be positioned within inner segment 2604, so that one or more inner segment apertures 2610 defined within inner segment can correspond/align with one or more component housing apertures 2676 defined within component housing 2675. Wrap 2650 can be wrapped around inner segment 2604, and proximal segment 2600 and distal segment 2602 can be connected to inner segment 2604 to complete construction of the device 100 as shown in FIG. 26. Wrap apertures 2655, as shown in FIG. 26, can correspond/align with the one or more inner segment apertures 2610 and the one or more component housing apertures 2676. As shown therein, when wrap 2650 is positioned around inner segment 2604, various components thereof (such as electrodes 122, 124, 126, 128 (shown in FIG. 26 and/or FIG. 28C), a distal conductor pad 2620, a proximal conductor pad 2700 (as shown in FIGS. 29D and 29E), and/or various wires or traces 980) can contact various portions of inner segment 2604, such as wires or traces 980, distal conductor contact 2612, one or more electrode contacts 2614, and/or a proximal conductor contact 2616.

FIG. 27 shows a perspective view of a portion of the device 100 shown in FIG. 27 that is generally assembled but for positioning of the wrap 2650 around inner portion 2604. As shown in FIG. 27, a pressure sensor (sensor 130), circuit module 140, and capacitor 762 are positioned inside device 100, with a partial cut-away view provided in FIG. 27 to see said components therein. FIG. 27 also shows a distal portion of a catheter 2750 configured for delivery over device 100 within a mammalian vasculature, whereby an optional fluid, such as saline, can be delivered therethrough so that a bolus of the fluid can pass over one or more sizing portions 120 and/or sensors 130 and be detected thereby, as generally referenced herein.

FIG. 28A shows a cross-sectional view of a portion of an exemplary device 100 of the present disclosure as shown along cross-section B-B in FIG. 28C. As shown therein, device 100, with wrap 2650 positioned thereon, includes a pressure sensor (sensor 130) within a component housing 2675 having one or more component housing apertures 2676 defined therein, and a transfer circuit 2680. FIG. 28B shows a cross-sectional view along cross section A-B shown in FIG. 28D, whereby various components are shown inside of device 100 with wrap 2650 positioned thereon. FIGS. 28C and 28D show side views, rotated 90° from one another, of distal portions of an exemplary device 100 of the present disclosure with a wrap 2650 positioned thereon, whereby electrodes 122, 124, 126, 128 and distal conductor pad 2620 are shown thereon.

FIG. 29A shows a perspective view of a portion of an exemplary device 100 of the present disclosure having a wrap 2650 positioned thereon, whereby electrodes 122, 124, 126, 128, distal conductor pad 2620, and proximal conductor pad 2700 are shown thereon. Such a view does not show the most distal portion and the most proximal portion of device 100. FIG. 29B shows a perspective view of an exemplary wrap 2650 having wrap apertures 2650 defined therein.

FIG. 29C is a magnified view of circular area A of wrap 2650 shown in FIG. 29D. As shown therein, various wires or traces 980 can terminate at one or more wire or trace termination points 982, whereby termination points 982 are configured to contact other componentry of device 100, such as one or more of electrodes 122, 124, 126, 128, distal conductor pad 2620, proximal conductor pad 2700, distal conductor contact 2612, electrode contact(s) 2614, and/or proximal conductor contact 2616, for example. An exemplary wrap 2650, as shown in the front and back (or top and bottom) views shown in FIGS. 29D and 29E, includes electrodes 122, 124, 126, 128, distal conductor pad 2620, proximal conductor pad 2700, various wires or traces 980, and one or more wrap apertures 2655 defined therein. Various wraps 2650 of the present disclosure can be connected to portions of device 100 (such as inner segment 2604 or a unitary core (conductive element or conductor 106) by way of, for example, one or more of adhesives, heat-shrinking, and/or mechanical connections.

FIGS. 30A-30E show views of portions of an exemplary component housing 2675 with various components therein. FIG. 30A shows a cut-away view of part of a component housing 2675 with a pressure sensor (sensor 130) and transfer circuit 2680 therein, with transfer circuit extending from within component housing 2675 via a transfer circuit aperture 2678 defined within component housing 2675. FIG. 30B shows a perspective view of half of a component housing 2675 with a pressure sensor (sensor 130), circuit module 104, and capacitor 762 therein, with a transfer circuit 2680 connected to one or more of said components, such as by way of wires or traces 980 shown in FIG. 30E. FIG. 30D is a cross-sectional view of part of the component housing 2675 shown in FIG. 30C, with various components therein. FIG. 30E shows a cross-sectional view of a component housing 2675 showing the components shown in FIG. 30B, noting that an exemplary transfer circuit 2680 of the present disclosure has one or more traces or wires 980 to facilitate electrical connection to other components as generally referenced herein.

In general, coronary guide wires need to be limited to an outer diameter of 0.014" so to be small enough to navigate to distal regions of coronary arteries and to accommodate coronary catheters which have lumens in that general size range. The guide wire cores therefore must be made of high modulus materials which take up as much of the 0.014" cross section as possible, so they are as stiff as possible for navigation purposes, and so they can enable delivery of the coronary catheters into tortuous anatomy.

Pressure sensing guide wires generally cannot be made with high modulus metals over most of the core cross section because they need to accommodate three (3) electrical conductors from the proximal to distal end of the device, somewhere within that cross section. As referenced herein, various device 100 embodiments of the present disclosure use four (4) electrodes (electrodes 122, 124, 126, and 128) to obtain sizing data, along with the use of a pressure sensor (sensor 130), and therefore a traditional device using these components would generally require at least seven (7) total conductors. Other sensors, such as a temperature sensor, would increase that number of conductors.

To be able to generate a device 100 configured as a guide wire having an outer diameter of 0.014" or less, useful to obtain sizing data and pressure data, Applicant's present disclosure includes various configurations of devices 100 using only one core (conductive element or conductor 104), whereby the combination of the ASIC (an exemplary circuit module 104) and a pad 200 (return patch) would allow for only a single core to be needed to operate several types of sensors, allowing for such devices 100 to be delivered similar to standard workhorse guide wires on the market today.

As referenced herein, exemplary proximal electrical units 700 of the present disclosure contain componentry that can perform various functions including, but not limited to:

a) powering of the distal circuitry (elements within, part of, and/or coupled to sensor substrate 760), such as by way of providing power from power source 702 to and through conductive element 106 to sensor substrate 760; and/or b) communicating with the distal circuitry to initiate the start of each sensory measurement phase, such as referenced in FIGS. 10, 11, and 13 and as generally referenced herein; and/or c) receiving data signal(s) 765 from the distal circuitry (within, part of, and/or coupled to sensor substrate 760) which contains diagnostic data as well as the data from the sensors (such as sizing portion 120 and/or sensors 130); and/or d) interpreting the data 765 coming from the sensors, such as correcting for non-linearities and offset errors in the sensory data, by way of using a microprocessor 900, for example; and/or e) storing device 100 specific information, such as sensor gain, sensor offset and device serial number, such as within memory 902 (an exemplary storage medium of the present disclosure); and/or f) communicating the resulting data to other devices, such as computers for visualization by medical professionals; and/or g) providing data that can be used for brand protection.

Functions listed above can be accomplished using a combination of analog and digital circuitry, such as a microcontroller (microprocessor 900) running a program which governs the operations of the entire proximal circuitry (within proximal electrical unit 700). Analog circuitry can be primarily responsible for the first three functions listed above, while digital circuitry can support the last four items on the list, for example. In an exemplary preferred embodiment, the proximal circuitry (proximal electrical unit 700) is housed within the handle portion of the guide wire (device 100), noting that the present disclosure also supports implementations where some part of the proximal circuitry, such as the analog circuitry, is placed within the handle while the digital circuitry is kept in the console, such as shown in an interpretation of FIG. 7 whereby element 700 (proximal electrical unit) comprises the handle and data acquisition and processing system 250 is connected/coupled to handle 700, with data acquisition and processing system 250 and handle 700 each including one or more component as referenced herein in connection with the same, such as, for example, power source 702, microprocessor 900, and/or memory 902. While the former option may provide for a simpler design (such as by requiring less additional componentry to operate device 100), the latter options allow a lower cost built by reducing the part count (overall componentry in the consumable/disposable portion of the medical device 100. For example, if an exemplary device 100 of the present disclosure is intended for one-time use (such as, for example, use with one patient), some or all proximal electrical unit 700 components could be included within data acquisition and processing system 250 versus a handle portion of device 100. In device embodiments 100 of the present disclosure whereby circuitry/componentry is included within proximal electrical unit 700 configured as a device 100 handle, housing around the proximal circuitry (an exemplary embodiment of proximal electrical unit 700) can keep it fluid impermeable and allow the entire medical device 100, including the proximal handle (an exemplary proximal electrical unit 700), to be sterilized using traditional methods, such as ethylene oxide sterilization.

In addition, and as generally referenced herein, an exemplary carrier wave 1000 of the present disclosure is the alternating current (AC) and/or oscillating direct current (DC) that is used to transmit the power 710 from the proximal circuitry (proximal electrical unit 700) to the distal circuitry (within, part of, and/or coupled to sensor substrate 760), and also to carry the data signal(s) 765 from the distal circuitry to the proximal circuitry. Carrier waves 1000 can be in the form of any waveshape that is chosen, but waves that are balanced, for example those having the long term mean value of zero, may be preferred. Sine waves, square waves, full triangular waves, clipped triangular waves and others are all acceptable options. For simplicity of the implementation, and in at least one embodiment of the present disclosure, the use of square waves maybe preferred.

Figure 31:
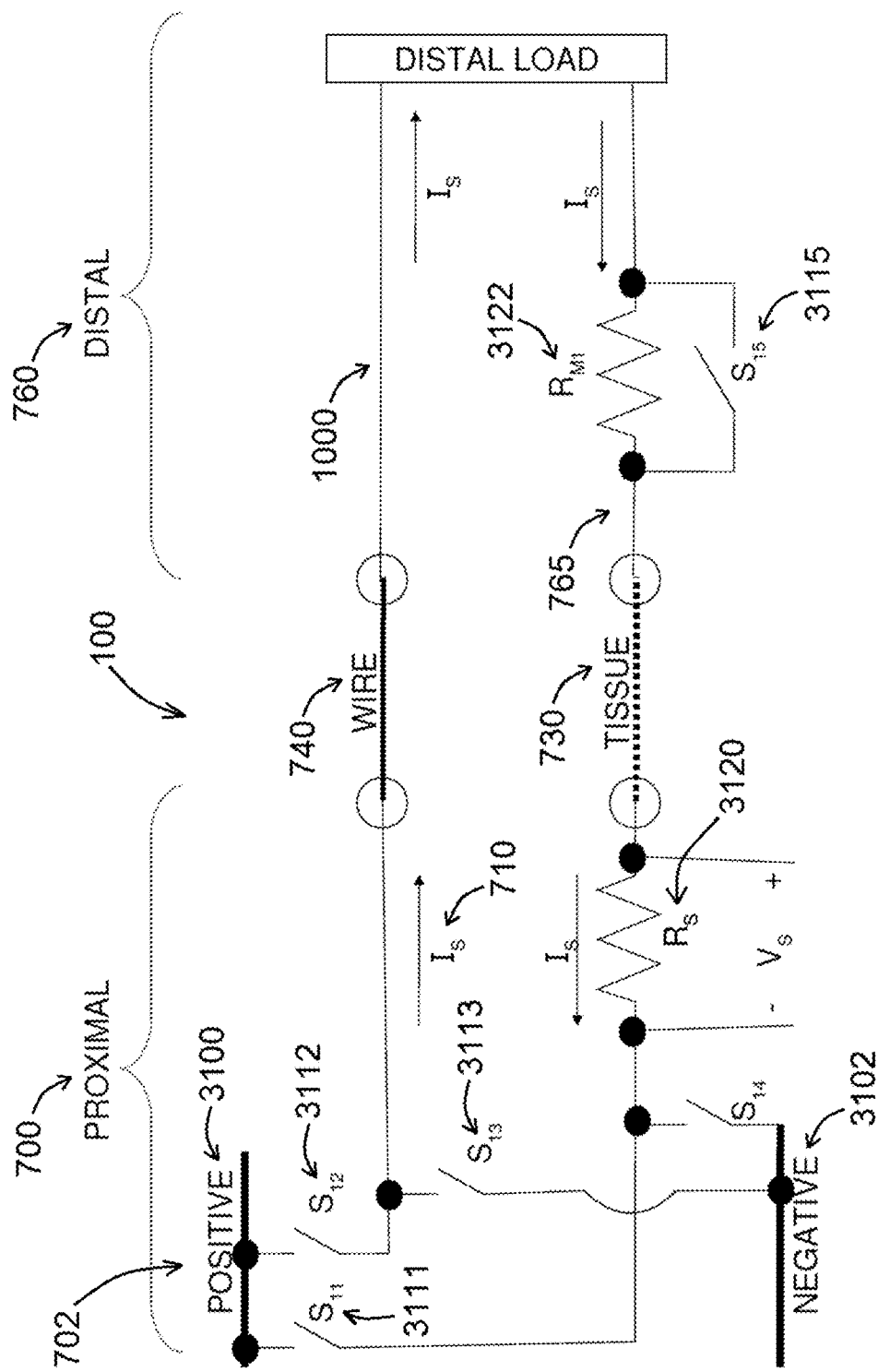
FIGS. 31 and 32 show device schematics, according to exemplary embodiments of the present disclosure.
Figure 32:
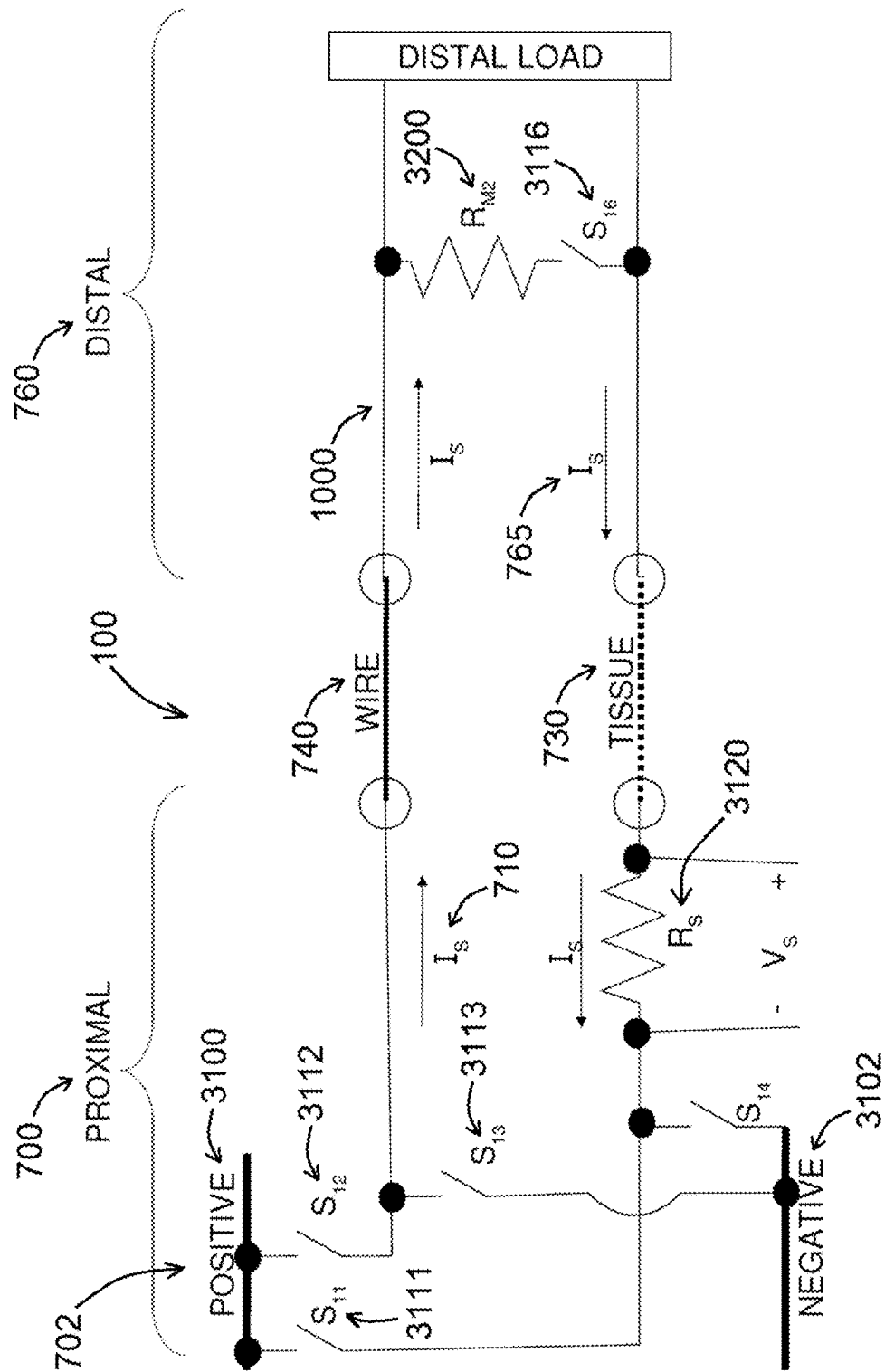

The production of the carrier wave 1000 is accomplished at the proximal side of device 100, which is where the power 710 is generated and transmitted from. This power 710 is received and used at the distal side (by componentry of sensor substrate 760). The modulation of the carrier wave 1000 is done by the distal circuitry to superimpose the data onto the carrier wave 1000, which is in turn demodulated by the proximal circuitry to recover the data sent by the distal circuitry. FIGS. 31 and 32 illustrate methods of production, modulation and demodulation of the carrier wave 1000, described in further detail below.

Production of an exemplary carrier wave 1000 by the proximal circuitry (of proximal electrical unit 700) starts with the drawing of electrical current from a power source 702 whose terminals are labeled as "positive" (positive terminal 3100) and "negative" (negative terminal 3102) in FIG. 31. During the first phase of the operation, switches $S_{12}$ (also referred to herein as switch 3112) and $S_{14}$ (also referred to herein as switch 3114) are closed while switches $S_{11}$ (also referred to herein as switch 3111) and $S_{13}$ (also referred to herein as switch 3113) are kept open. In this phase, the electrical current (power 710) coming from the positive terminal 3100 of power supply 702 flows first through the switch $S_{12}$ (switch 3112) and then through guide wire 740 to reach to the distal load. Passing through the distal load, the same current, which is now labeled as $I_s$ in FIGS. 31 and 32, passes through first the switch $S_{15}$ (also referred to herein as switch 3115), which is usually closed, and then through the tissue 730 to reach back to the proximal side (proximal electrical unit 700). As generally referenced herein, an overall device 100 of the present disclosure may be comprised as a guide wire, with the proximal electrical unit 700 being referred to as the "proximal side" of the device 100 (configured as a guide wire) and the sensor substrate 760 being referred to as the "distal side" of the device 100 (configured as a guide wire). Afterwards, the current (power 710) goes through the resistor $R_s$ (also referred to herein as resistor 3120) and the switch $S_{14}$ (switch 3114) to reach to the negative terminal 3102 of the battery (an exemplary power source 702). It is noted that during this first phase of the carrier wave 1000 generation, the "wire" (part of guide wire 740 distal to proximal electrical unit 700) is a positive potential while the tissue 730 is at a negative potential.

In the second phase of an exemplary carrier wave 1000 generation, the switches $S_{12}$ (switch 3112) and $S_{14}$ (switch 3114) are kept open while switches $S_{11}$ (switch 3111) and $S_{13}$ (switch 3113) are closed. This configuration reverses the direction of $I_s$ since the current coming from the positive terminal 3100 of the power supply 702 goes through $S_{11}$ (switch 3111) and $R_s$ (resistor 3120) to reach the tissue 740. This current then goes through the switch $S_{15}$ (switch 3115), the distal load, the "wire" (the part of guide wire 740 between the proximal electrical unit 700 and the sensor substrate 760) and finally the switch $S_{13}$ (switch 3113) to reach to the negative terminal 3102. During the second phase of an exemplary carrier wave generation 1000, the "wire" (the part of guide wire 740 between the proximal electrical unit 700 and the sensor substrate 760) is a negative potential while the tissue 740 is at a positive potential. This alternation of the both potential and the direction of the current $I_s$ assures that the carrier wave 1000 retains its AC nature, for example.

The modulation of the carrier wave 1000 can be done using various different arrangements, as illustrated in FIGS. 31 and 32. The arrangement shown in FIG. 31 utilizes a series resistor, $R_{M1}$ (resistor 3122) to modulate the carrier wave 1000. Briefly, when the switch $S_{15}$ (switch 3115) is closed, the only resistances that the current $I_S$ faces are the resistance of the distal load, $R_L$ and the sense resistor $R_S$, giving the total resistance value of $R_L+R_S$. If the voltage of the power supply 702 is $V_P$, then the current $I_S$ can be found using the Ohm's law:

$$I_{S1}=V_P/(R_L+R_S) \quad \text{[Equation 2]}$$

When the switch $S_{15}$ (switch 3115) is open, the current $I_S$ must go through the resistances $R_L$, $R_{M1}$ and the $R_S$, giving the total resistance value of $R_L+R_{M1}+R_S$. Again using the Ohm's law, the new value of the current $I_S$ can be determined to be:

$$I_{S2}=V_P/(R_L+R_{M1}+R_S) \quad \text{[Equation 3]}$$

Comparing Equation 2 and Equation 3, one can conclude that the $I_{S2}$ is less than $I_{S1}$, since the denominator of Equation 3 is larger the denominator of the Equation 2.

The voltage drop $V_S$ over the resistor $R_S$ (resistor 3120) is can be calculated for both values of the current $I_S$ as follows:

$$V_{S1}=R_S*I_{S1}=(V_P*R_S)/(R_L+R_S) \quad \text{[Equation 4]}$$

$$V_{S2}=R_S*I_{S2}=(V_P*R_S)/(R_L+R_{M1}+R_S) \quad \text{[Equation 5]}$$

Again it can be inferred that $V_{S2}$ is less than $V_{S1}$.

Modulation of the carrier wave is accomplished by opening and closing of the switch $S_{15}$. To transmit a data bit corresponding to a "1", the distal circuitry closes the switch $S_{15}$, which increases the value of the current Is to a value of $I_{S1}$ and the VS increases to $V_{S1}$, which detected by the proximal circuitry as data bit of "1". Conversely, the opening of the switch $S_{15}$ by the distal circuitry reduces the $I_S$ to $I_{S2}$ and $V_S$ to $V_{S2}$, leading to the detection of the "zero" bit by the proximal circuitry.

To obtain a traditional modulation index of 10%, it is preferred that the values of $R_{M1}$ and $R_S$ be chosen such that the ratio of $(I_{S1}-I_{S2})/I_{S1}=0.1$.

The arrangement shown in FIG. 31 has the advantage of allowing the power flow to the distal load all times, regardless of the transmission of a "one" or a "zero", although some reduction of power is experienced during the transmission of a zero. It is possible to reverse the designations of the zero and one, for example, so that $S_{15}$ is closed to send a "zero" and opened to send a "one".

The schematic that is shown in FIG. 32 utilizes a shunt resistor, $R_{M2}$ (resistor 3200), to modulate the carrier wave 1000. Briefly, when the switch $S_{16}$ (switch 3116) is opened, the current $I_S$ has only a single path to take when it travels in the distal circuitry which has the resistors $R_L$ and $R_S$.

$$I_{S1}=V_P/(R_L+R_S) \quad \text{[Equation 6]}$$

and $$V_{S1}=R_S*I_{S1}=(V_P*R_S)/(R_L+R_S) \quad \text{[Equation 7]}$$

However, when the switch $S_{16}$ (switch 3116) is closed, the current has two paths to take, one through the distal load and the other through the resistor $R_{M2}$, which reduces the total resistance.

$$I_{S2}=V_P/(R_L*R_{M2}/(R_L+R_{M2})+R_S) \quad \text{[Equation 8]}$$

and $$V_{S2}=R_S*I_{S2}=(V_P*R_S)/(R_L*R_{M2}/(R_L+R_{M2})+R_S) \quad \text{[Equation 9]}$$

In this schematic, switch $S_{16}$ (switch 3116) is usually kept open, not closed as in the case of first schematic described earlier, to allow the full power to be delivered to the distal load and not be lost over the shunt resistor $R_{M2}$. Again the current $I_S$ and the corresponding sense voltage $V_S$ are larger when the switch $S_{16}$ is closed. Choice of the switch closure to represent a zero or a one is also arbitrary in this schematic (FIG. 32) as it was with schematic (FIG. 31).

The first schematic (shown in FIG. 31) is more appropriate for a situation where the noise is low, and the reliable transmission can be accomplished with a low modulation index since the modulation accomplished by a further reduction of the amplitude of the carrier wave 1000. For example, if the noise is only few percent of the carrier wave 1000 amplitude, then a 10% reduction in the carrier wave 1000 amplitude can easily be detected by the proximal circuitry. Then it is preferred to use the first schematic (shown in FIG. 31) as it reduces the power delivered to the distal load by approximately 10% during the times that the switch $S_{15}$ is closed.

The second schematic (shown in FIG. 32) is preferred when the inherent noise level is high. This schematic increases uses a modulation by increasing the current and the sense voltage to overcome the noise. However, it has the trade-off of dramatically reducing the current being supplied to the distal load during the data transmission.

Exemplary integrated circuits (ICs or ASICs, referred to herein as exemplary circuit modules 104) may include various components contained within sensor substrates 760 of the present disclosure. Furthermore, various circuit modules 104 of the present disclosure can be configured and/or operable to perform the following tasks/functions, such as, but not limited to:

a) Rectification of the AC power coming from the proximal circuit (proximal electrical unit 700) to generate DC power that is necessary for the operation of the distal circuitry (of, within, or coupled to sensor substrate 760); and/or b) Regulation of the DC power to reduce ripples and provide constant voltage supply that is needed by the components of the distal circuitry; and/or c) Modulation of carrier wave 1000 for the transmission of the data from the distal circuitry to the proximal circuitry; and/or d) Detection of the interruption of the power by the proximal circuitry, which in turn indicates that it is safe for the distal circuitry to collect data using the sensors (sizing portion 120 and/or sensor(s) 130) that are present at the distal circuitry; and/or e) Govern the operation of all the circuits and sensors in the distal tip, including the power storage capacitor (capacitor 762), pressure sensor (an exemplary sensor 130), temperature sensor (another exemplary sensor 130), and the impedance sensor(s), such as electrodes 122, 124, 126, 128; and/or f) Generate diagnostic information that can be sent back to the proximal circuitry; and/or g) Produce necessary offset voltages to the sensors and the onboard amplifiers (such as amplifiers 914); and/or h) Turn on and off the isolation switches (such as switches 930, 932, and/or other switches referenced herein) during and after the sensory measurements respectively to reduce the interference of the carrier wave 1000 to the data from the transducers; and/or i) Produce excitation that is necessary for the operation of the sensors (such as electrodes 126, 128), including the AC excitation to the electrodes 126, 128 of the impedance sensor (sizing portion 120) and the strain gauges residing the bridge circuit of the pressure sensor as well as the temperature sensor; and/or j) Amplify the signals coming back from the sensors (such as, for example, by way of directing and/or regulating operation of one or more amplifiers 914); and/or k) Sample the signals coming back from the sensors at the correct instance; and/or l) Convert the analog signals coming from the sensors into a digital format (such as, for example, by way of direction and/or regulating operation of analog to digital converter 922); and/or m) Store the digital sensor data, such as within memory 964 (an exemplary storage medium of the present disclosure that can be connected to circuit module 104 and/or other components of sensor substrate 760, whereby memory 964 can store data until it can be transmitted to the proximal circuitry; and/or n) Transmit data to the proximal circuitry (such as, for example, by way of direction and/or regulating operation of wired or wireless communication module 600 or another part of device 100 configured to transmit data, as referenced herein); and/or o) Interface with the optional radio frequency (RF) components to recover power being transmitted by the proximal circuitry using radio frequency electromagnetic waves;

p) Interface with the optional RF components to transmit data using radio frequency electromagnetic waves to the proximal circuitry;

q) Recognize that power from the proximal electrical unit 700 has temporarily stopped flowing to the conductor 106; and/or r) Direct power from the proximal electrical unit 700 to temporarily stop being delivered to the conductor 106.

As noted above, one or more of the following functions/tasks can be completed using componentry inherent within circuit module 104 and/or componentry, such as shown in the various figures in connection with sensor substrate 760, in communication with circuit module 104.

As generally referenced herein, and in at least one embodiment of using a device 100 of the present disclosure, portions of a pressure sensor 130 (such as the half Wheatstone bridge referenced herein) can be used as a thermistor, or a separate thermistor (sensor) can be used to obtain temperature data, such as a threshold temperature based upon, for example, the temperature of an injected bolus or the warming or cooling of said sensor based upon the temperature of blood. Such a threshold temperature can trigger operation of one or more of sizing portion 120 and/or sensors 130 to obtain measurements, such as by way of direction of circuit module 104 after receiving the temperature data. The operation trigger can also be made after the circuit module 104 delivers a signal via carrier wave 1000 over the power signal to direct the proximal electrical unit 700 to temporarily stop delivering power to the sensor substrate 760 via conductor 106. Alternatively, the circuit module 106 can operate to turn power off while data is obtained and/or transmitted back to the proximal electrical unit 700.

Figure 33:
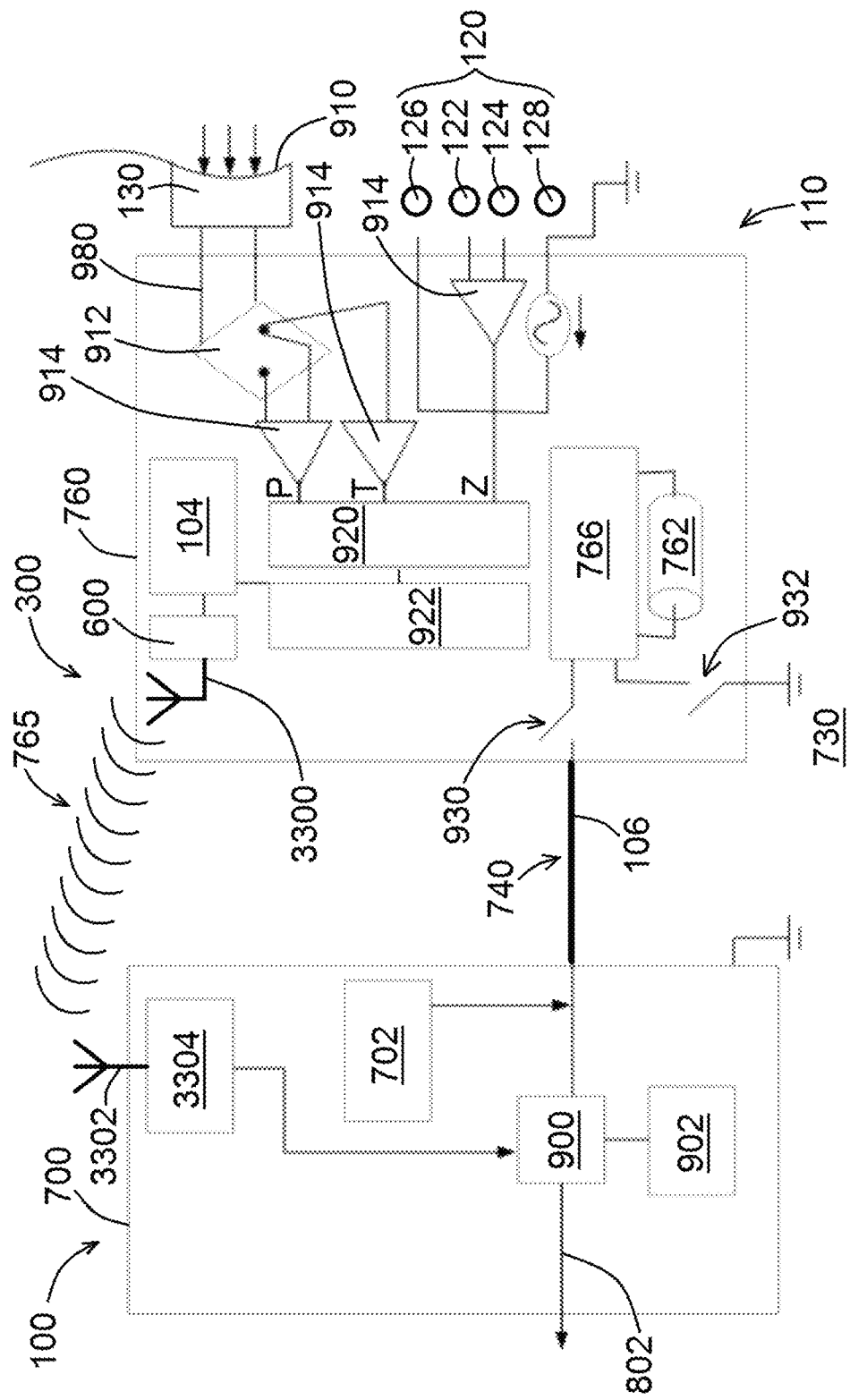
FIGS. 33 and 34 show devices and systems useful to obtain data, according to exemplary embodiments of the present disclosure.

In at least one embodiment of a device 100 of the present disclosure, the distal componentry (of or coupled to sensor substrate 760) is powered via the electrical current $I_s$ that is delivered through the circuit formed by the guide wire 740 (part of device 100) and tissue 730 while the data is transmitted electromagnetically, as shown in FIG. 33. In such an embodiment, the carrier wave 1000 is not modulated by the distal end componentry of device 100. However, it is periodically interrupted to indicate to the distal circuitry that it is safe to make measurements from the sensors (such as sizing portion 120 and/or one or more sensors 130) without having interference from the carrier wave 1000. The resulting data is sent back to the proximal electrical unit (700) using radio frequency electromagnetic waves 3350, as shown in FIG. 33 as being transmitted from a distal portion antenna 3300 of or coupled to wired or wireless communication module 600 to a proximal portion antenna 3302 of a receiver 3304 of, within, or coupled to proximal electrical unit 700. Transmission can be done at any frequency that is suitable and permitted by regulatory agencies, but frequencies where the absorption is high due to tissue 730 should be avoided. Furthermore, higher frequencies require shorter wavelengths, hence shorter antenna 3300, 3302 lengths are preferred in various embodiments, However, at high frequencies, the absorbance of tissue 730 may increase. Although, frequencies in the range of 10 KHz to 100 MHz can be used, frequencies around 64 MHz may be preferred depending on the embodiment used.

Data transmission can be accomplished by any of the known modulation schematics referenced herein, including amplitude modulation, frequency modulation, and pulse position modulation, which are examples of the modulation schematics that can be used for the transmission of the sensory data in analog format using time division multiplexing, for example. Similarly, amplitude shift keying, frequency shift keying and phase shift keying can be used for the transmission of the digital data. Other data techniques that can be used for transmission of information, such frequency division multiplexing are all within the scope of the present disclosure.

This schematic shown in FIG. 33 also allows additional data to be sent to the distal unit from the proximal unit using the same RF channel.

Figure 34:
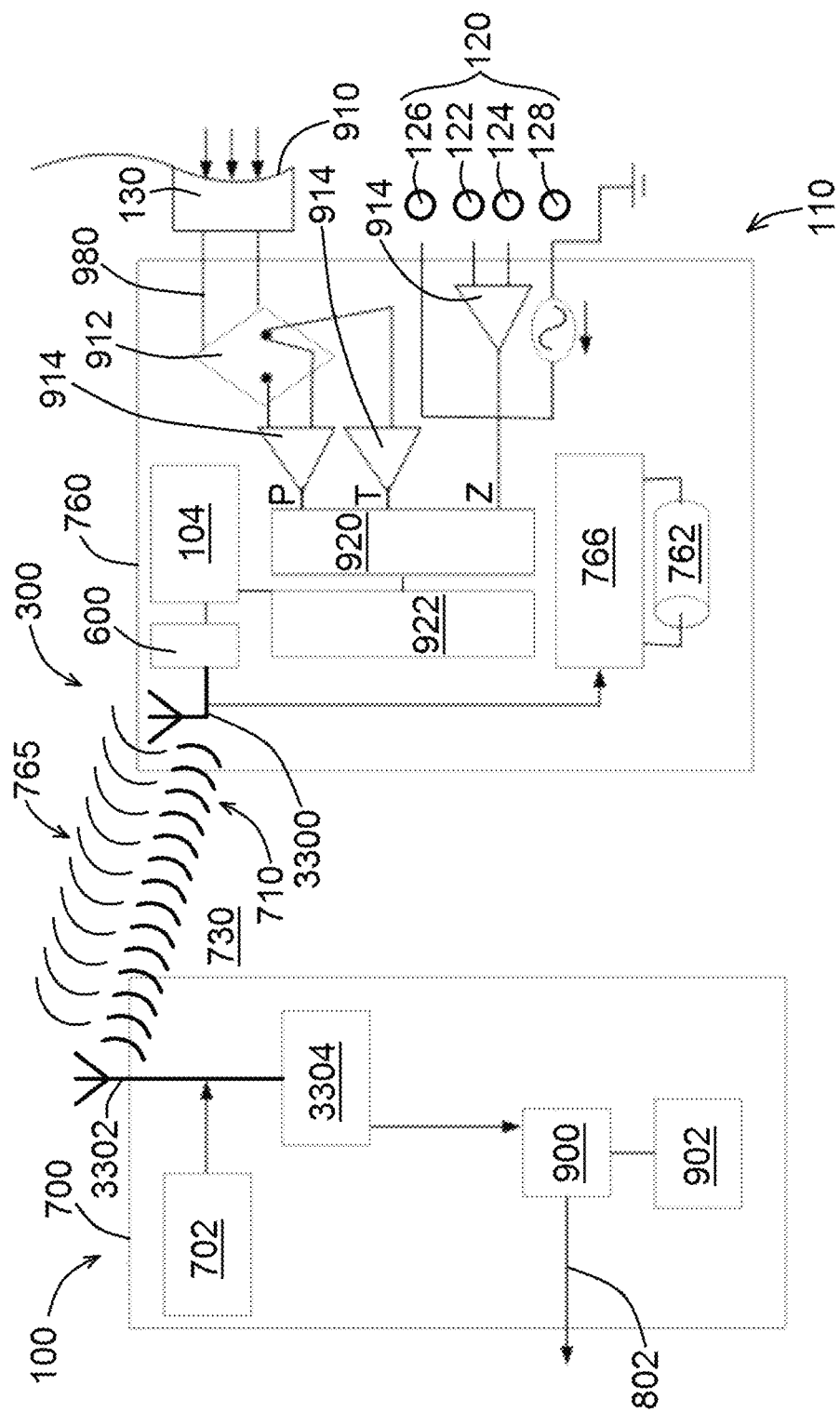

In an additional embodiment of the present disclosure, the distal tip is powered via RF power delivered through the tissue 730 and the data is also transmitted back electromagnetically, as it is shown in FIG. 34. In this case, there is no need for the electrical loop formed by the guide wire 740 and the tissue 730, and the isolation switches (switches 930, 932) are eliminated from the distal circuitry. Furthermore, since no carrier wave 1000 is sent from the proximal circuitry, there is neither a modulator on the distal circuitry nor a demodulator on the proximal circuitry. Instead, two RF units, one located in the proximal circuitry and labeled as receiver 3304 and the other in the distal circuitry and labeled as wired or wireless communication module 600 are used to transmit the power 710 from the proximal unit to the distal unit and to return data signals 765 from the distal circuit to the proximal circuitry.

Although it is possible to build custom circuits for RF based power and data transmission, it is also possible to use RFID chips that operate at different frequencies ranging from 13 MHz to 900 MHz. In such an embodiment, the RFID device located on the distal portion of the guide wire (namely wired or wireless communication module 600 having an antenna 3302) would recover the power from the incoming RF signal, and provide that the circuit module 104 to power it. An RFID chip would also then return the data back to the proximal unit.

In order to transmit the power efficiently and to receive the data reliably, the proximal circuitry or at least the antenna 3302 of receiver 3304 may need to be positioned near the distal tip of the guide wire.

Circuitry that is located in the distal tip (of, within, or coupled to sensor substrate 760) scans the sensors (such as sizing portion 120 and/or other sensors 130) that are present on the medical device 100, and samples them one by one at the appropriate time. The time to activate the sensors to produce the transducer data is determined by the operation of the proximal circuitry (of, within, or coupled to proximal electrical unit 700). The proximal circuitry periodically interrupts the overall transmission of the power, as generally referenced herein, to the distal circuitry by suspending the generation of the carrier wave 1000. The distal circuitry continuously monitors the availability of the carrier wave 1000 and interprets the absence of the carrier wave 1000 as an indication that it is time to activate the next sensor in line and to make a measurement. The absence of the carrier wave 1000 serves not only serves as a trigger for the distal circuitry to switch into the measurement mode (whereby sizing portion 120 and/or sensor(s) 130 operate to obtain sizing, pressure, and/or temperature data), but also allows for the creation of an environment that is void of electrical interference that is induced in the tissue 730 by the carrier wave 1000. The distal circuitry possesses a counter (such as within or controlled by circuit module 104) that allows it to cycle through the sensors on board to make measurements. The measurement period that is produced by the suspension of the carrier wave 1000 proximal is sufficiently long for the distal circuitry to activate the sensors and the associated electronic amplifiers 914, wait for them to stabilize, obtain a reliable measurement, and convert the resulting data into a digital format using the on board analog-to-digital converter (ADC) 922. Finally, the resulting data is transmitted back to the proximal circuitry by the modulation of the carrier wave 1000 once the carrier wave 1000 is restored by the proximal circuitry.

Various devices 100 and/or systems 300 of the present disclosure may use various formulas and/or algorithms, such as Ohm's Law and/or a distance between two electrodes (such as a distance between two detection electrodes 122, 124) used to detect within an electric field, one or more saline injections, etc., as described in one or more of the following references, wherein said devices 100 and/or systems 300 are configured to perform one or more of the following procedures/tasks:

(a) determining the size (cross-sectional area or diameter, for example) of a mammalian luminal organ, parallel tissue conductance within a mammalian luminal organ, and/or navigation of a device within a luminal organ, such as described within U.S. Pat. No. 7,454,244 to Kassab et al., U.S. Pat. No. 8,114,143 to Kassab et al., U.S. Pat. No. 8,082,032 to Kassab et al., U.S. Patent Application Publication No. 2010/0152607 of Kassab, U.S. Patent Application Publication No. 2012/0053441 of Kassab, U.S. Patent Application Publication No. 2012/0089046 of Kassab et al., U.S. Patent Application Publication No. 2012/0143078 of Kassab et al., and U.S. Patent Application Publication No. 2013/0030318 of Kassab, the entire contents of which are hereby incorporated into the present disclosure by reference;

(b) determining the location of one or more body lumen junctions and/or profiles of a luminal organ, such as described within U.S. Patent Application Publication No. 2009/0182287 of Kassab, U.S. Patent Application Publication No. 2012/0172746 of Kassab, U.S. Pat. No. 8,078,274 to Kassab, and U.S. Pat. No. 8,632,469 of Kassab, the entire contents of which are hereby incorporated into the present disclosure by reference;

(c) ablating a tissue within a mammalian patient and/or removing stenotic lesions from a vessel, such as described within U U.S. Patent Application Publication No. 2009/0182287 of Kassab, U.S. Patent Application Publication No. 2010/0222786 of Kassab, U.S. Patent Application Publication No. 2013/0282037 of Kassab, and U.S. Pat. No. 8,465,452 of Kassab, the entire contents of which are hereby incorporated into the present disclosure by reference;

(d) determining the existence, potential type, and/or vulnerability of a plaque within a luminal organ, such as described within U.S. Patent Application Publication No. 2010/0152607 of Kassab, U.S. Patent Application Publication No. 2011/0034824 of Kassab, and U.S. Pat. No. 7,818,053 to Kassab, the entire contents of which are hereby incorporated into the present disclosure by reference;

(e) determining phasic cardiac cycle measurements and determining vessel compliance, such as described within U.S. Pat. No. 8,185,194 to Kassab and U.S. Pat. No. 8,099,161 to Kassab, the entire contents of which are hereby incorporated into the present disclosure by reference;

(f) determining the velocity of a fluid flowing through a mammalian luminal organ, such as described within U.S. Pat. No. 8,078,274 to Kassab, U.S. Patent Application Publication No. 2010/0152607 of Kassab, U.S. Patent Application Publication No. 2012/0053441 of Kassab et al., and U.S. Patent Application Publication No. 2012/0089046 of Kassab et al., the entire contents of which are hereby incorporated into the present disclosure by reference;

(g) sizing of valves using impedance and balloons, such as sizing a valve annulus for percutaneous valves, as described within U.S. Patent Application Publication No. 2013/0317392 of Kassab and U.S. Pat. No. 8,406,867 of Kassab, the entire contents of which are hereby incorporated into the present disclosure by reference;

(h) detecting and/or removing contrast from mammalian luminal organs, such as described within U.S. Pat. No. 8,388,604 to Kassab, the entire contents of which are hereby incorporated into the present disclosure by reference;

(i) determining fractional flow reserve, such as described within U.S. Patent Application Publication No. 2011/0178417 of Kassab and U.S. Patent Application Publication No. 2011/0178383 of Kassab, the entire contents of which are hereby incorporated into the present disclosure by reference; and/or (j) to place leads within a mammalian luminal organ, such as by using a device 100 of the present disclosure to navigate through a mammalian luminal organ to a location of interest, and using device 100 and/or a second device to place a lead within said luminal organ.

In addition to the foregoing, various devices 100 of the present disclosure, and various other impedance devices as described in one or more of the aforementioned patents and/or patent applications (such as tetrapolar devices), may be operable to perform one or more of ablation of relatively small veins, such as to navigate through mammalian luminal organs for Endovascular Laser Therapy (EVLT) for treatment of venous insufficiency of varicose veins (cosmetic procedures), and/or to measure ureter stenosis at different levels, including at level of ureter emerging from the kidney, as well as to measure the urethra/urinary bladder junction, strictures of abnormal congenital ureter in children, enlargement of ureter in pregnant women due to compression of the uterus against ureter, trauma with pelvic fracture, and other urological conditions.

While various embodiments of impedance devices with integrated circuit modules and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An impedance device, comprising:
an elongated body configured for at least partial insertion into a mammalian luminal organ of a patient, the elongated body having a first conductor extending therethrough;
a proximal electrical unit operably connected to the elongated body and configured to deliver power along the first conductor; and
a single, flexible sensor substrate located at or near a distal end of the elongated body and configured to wrap around at least part of the elongated body, the sensor substrate comprising each of a circuit module, a sizing portion, and a pressure sensor thereon, wherein the circuit module is operably coupled to the sizing portion and the pressure sensor that are powered directly or indirectly from the power delivered through the first conductor, the circuit module configured to:
a) direct operation of the sizing portion to obtain sizing data;
b) direct operation of the pressure sensor to obtain pressure data; and
c) transmit the sizing data and/or the pressure data to the proximal electrical unit.

2. The impedance device of claim 1, wherein the sensor substrate further comprises a capacitor configured to obtain the power from the proximal electrical unit.

3. The impedance device of claim 2, wherein the sensor substrate further comprises a distal power source, the distal power source configured to charge the capacitor.

4. The impedance device of claim 1, further comprising:
a wrap configured to wrap around at least part of the elongated body at a first location.

5. The impedance device of claim 4, wherein the sizing portion comprises a plurality of electrodes configured to obtain the sizing data, and wherein the plurality of electrodes are coupled to or formed as part of the wrap.

6. The impedance device of claim 1, wherein the proximal electrical unit is further configured to process the sizing data and/or the pressure data from the circuit module.

7. The impedance device of claim 1, wherein the first conductor comprises a single conductor, and wherein the circuit module is operable to direct operation of the sizing portion to obtain sizing data, to direct the pressure sensor to obtain pressure data, and to transmit the sizing data and/or the pressure data to the proximal electrical unit using the power delivered along the first conductor.

8. The impedance device of claim 1, wherein the circuit module is powered by a distal power source of the sensor substrate, the distal power source configured to power the circuit module using the power delivered through the first conductor and/or from a capacitor coupled to the distal power source that is configured to receive the power delivered through the first conductor.

9. The impedance device of claim 1, wherein the sizing portion comprises a pair of detection electrodes positioned in between a pair of excitation electrodes, the pair of excitation electrodes are configured to generate an electric field detectable by the pair of detection electrodes.

10. The impedance device of claim 1, wherein the sizing portion and the pressure sensor are each operably connected to a multiplexer positioned upon or within the sensor substrate.

11. The impedance device of claim 1, wherein the sensor substrate transmits the sizing data and/or the pressure data to the proximal electrical unit by way of a metallic element coupled to the sensor substrate, wherein the metallic element is configured to transmit the sizing data and/or the pressure data through tissue adjacent to the mammalian luminal organ to a pad positioned upon skin of the patient.

12. The impedance device of claim 1, wherein the elongated body further has a second conductor extending therethrough, wherein the power is delivered from the proximal electrical unit to the sensor substrate using the first conductor, and wherein the sizing data and/or the pressure data is transmitted from the sensor substrate to the proximal electrical unit using the second conductor.

13. The impedance device of claim 1, wherein the sensor substrate further comprises a temperature sensor, and wherein the circuit module is further operable and/or configured to direct the temperature sensor to obtain temperature data and to transmit the temperature data to the proximal electrical unit.

14. The impedance device of claim 1, wherein the elongated body and the sensor substrate each have an outer diameter of 0.014" or less.

15. The impedance device of claim 1, wherein the circuit module is operable and/or configured to transmit the sizing data and/or the pressure data to the proximal electrical unit by directing operation of a wireless communication module configured to wirelessly transmit the sizing data and/or the pressure data to the proximal electrical unit or a component coupled thereto.

16. The impedance device of claim 1, wherein the impedance device forms part of a system, the system further comprising:
a pad configured for attachment to skin of the patient and further configured to receive the sizing data and/or the pressure data from the sensor substrate through tissue of the patient.

17. An impedance device, comprising:
an elongated body configured for at least partial insertion into a mammalian luminal organ of a patient, the elongated body having a first conductor extending therethrough;
a proximal electrical unit operably connected to the elongated body and configured to deliver power along the first conductor; and
a single, flexible sensor substrate located at or near a distal end of the elongated body and configured to wrap around at least part of the elongated body, the sensor substrate comprising each of a circuit module, a sizing portion, and a pressure sensor thereon, wherein the circuit module is operably coupled to the sizing portion and the pressure sensor that are powered directly or indirectly from the power delivered through the first conductor, the circuit module configured to:
a) direct operation of the sizing portion to obtain sizing data;
b) direct operation of the pressure sensor to obtain pressure data; and
c) transmit the sizing data and/or the pressure data to the proximal electrical unit;
wherein a) and b) are performed upon the circuit module identifying that power through the single conductor from the proximal electrical unit has temporarily stopped.

18. The impedance device of claim 17, wherein the proximal electrical unit is further configured to process the sizing data and/or the pressure data from the circuit module, and wherein the circuit module is also coupled to a temperature sensor, and wherein the circuit module is operable and/or configured to direct operation of the temperature sensor to obtain temperature data.

19. A method, comprising:
inserting a portion of an impedance device into a luminal organ of a patient, the impedance device comprising:
an elongated body configured for at least partial insertion into the luminal organ, the elongated body having a first conductor extending therethrough,
a proximal electrical unit operably connected to the elongated body and configured to deliver power through the first conductor, and
a single, flexible sensor substrate located at or near a distal end of the elongated body and configured to wrap around at least part of the elongated body, the sensor substrate comprising each of a circuit module, a sizing portion, and a pressure sensor thereon, the circuit module configured to direct operation of the sizing portion to obtain sizing data and the pressure sensor to obtain pressure data and further configured to transmit the sizing data and/or the pressure data to the proximal electrical unit by way of the elongated body;

operating the impedance device to obtain the sizing data and the pressure data within the luminal organ;

transmitting one of the sizing data or the pressure data to the proximal electrical unit; and if the sizing data was transmitted to the proximal electrical unit, transmitting the pressure data to the proximal electrical unit, or if the pressure data was transmitted to the proximal electrical unit, transmitting the sizing data to the proximal electrical unit.

20. The method of claim 19, wherein the sizing data and/or the pressure data is transmitted to the proximal electrical unit by first transmitting the sizing data and/or the pressure data through tissue of the patient to a pad positioned upon the patient's skin, wherein the pad is operably connected to the proximal electrical unit.

* * * * *